United States Patent [19]

Noyori et al.

[11] Patent Number: 4,845,282

[45] Date of Patent: Jul. 4, 1989

[54] PROCESS FOR PROSTAGLANDIN $E_1$ PRODUCTION, AND NOVEL DELTA 7-PROSTAGLANDINS E AND 7-HYDROXYPROSTAGLANDINS E

[75] Inventors: Ryoji Noyori, Nisshin; Masaaki Suzuki, Nagoya; Toshio Kawagishi, Minamiashigara; Seizi Kurozumi, Kobubunji, all of Japan

[73] Assignee: Teijin Limited, Osaka, Japan

[21] Appl. No.: 147,124

[22] Filed: Jan. 21, 1988

Related U.S. Application Data

[62] Division of Ser. No. 438,379, Nov. 1, 1982, abandoned.

[30] Foreign Application Priority Data

Nov. 13, 1981 [JP] Japan ................................. 56-180954
Dec. 3, 1981 [JP] Japan ................................. 56-193721
Dec. 7, 1981 [JP] Japan ................................. 56-195590

[51] Int. Cl.$^4$ .......................................... C07C 177/00
[52] U.S. Cl. ..................................... 562/500; 547/422; 547/466; 547/478; 556/441; 556/442; 560/53; 560/118; 560/121; 562/463; 562/503
[58] Field of Search ........................ 560/121, 118, 53; 562/503, 463, 500; 549/422, 478, 466; 556/441, 442

[56] References Cited

U.S. PATENT DOCUMENTS 3,435,053  3/1969  Real ..................................... 560/121

OTHER PUBLICATIONS

Fiereu et al, Reagents for Organic Synthesis p. 1183 (1969).
House, Modern Synthetic Reacton p. 173 (1972).
Suzuki et al, Tet Letters. 23 (39) 4057 (1982).

*Primary Examiner*—Robert Gerstl
*Attorney, Agent, or Firm*—Sherman and Shalloway

[57] ABSTRACT

The present invention provides an industrially very advantageous process for producing prostaglandins $E_1$ with fewer steps and in higher yield. The process comprises reacting a 7-hydroxyprostaglandin E with a reactive derivative of an organic sulfonic acid in the presence of a basic compound to form the corresponding 7-organic sulfonyloxyprostaglandin E, treating the resulting 7-organic sulfonyloxyprostaglandin E, after or without isolation, in the presence of a basic compound to form a $\Delta^7$-prostaglandin E, thereafter selectively reducing the carbon-carbon unsaturated bond existing on the α-chain. Some of the 7-hydroxyprostaglandins E and $\Delta^7$-prostaglandins E used in the process are novel compounds.

12 Claims, No Drawings

PROCESS FOR PROSTAGLANDIN E₁ PRODUCTION, AND NOVEL DELTA 7-PROSTAGLANDINS E AND 7-HYDROXYPROSTAGLANDINS E

This application is division of application Ser. No. 438,379, filed Nov. 1, 1982, now abandoned.

This invention relates to a process for the production of prostaglandins $E_1$ and to novel $\Delta^7$-prostaglandins E and 7-hydroxyprostaglandins E.

Prostaglandin $E_1$ is a compound having unique biological activities such as platelet aggregation inhibiting activity and antihypertensive activity. It is a naturally occurring substance which has recently been used as a peripheral circulation improver in the field of medical therapy.

Various processes for the production of prostaglandin $E_1$ (hereinafter "prostaglandin" will sometimes be referred to as "PG" for brevity) are known, and described, for example, in J. B. Bindra et al., "Prostaglandin Synthesis", Academic Press (1977), and Abhijit Mitra, "The Synthesis of Prostaglandins", John Wiley & Sons (1977).

Some typical known processes are shown below. (i) Biosynthesis from dihomo-γ-linolenic acid [D. A. Dorp et al., Biochem. Biophys. Acta, 90, 204 1964)]; (ii) intramolecular Aldol condensation of a nitroalkane derivative, followed by optical resolution of the condensate [E. J. Corey et al., J. Amer. Chem. Soc., 91, 535 (1969)]; (iii) Michael addition of an organometallic compound to a 2-substituted-2-cyclopentenone derivative [C. J. Sih et al., J. Amer. Chem. Soc., 95, 1676 (1973); and A. F. Kluge et al. J. Amer. Chem. Soc., 94, 7827 (1972)]; and (iv) selective hydrogenation of the double bond at the 5-position of protected prostaglandin $E_2$ or $F_{2\alpha}$ [E. J. Corey et al., J. Amer. Chem. Soc., 92, 2586 (1970)].

According to the biosynthetic method (i), the yield of the desired product from the starting dihomo-γ-linolenic acid is extremely low, and therefore, the resulting $PGE_1$ is difficult to obtain in purified form from the reaction mixture containing by-products. On the other hand, the processes (ii) to (iv) based on chemical synthesis require many steps in obtaining the starting materials. Even if such a starting material is easily obtained, these processes still have the defect that the yield of the desired prostaglandin $E_1$ from the starting material is very low.

Heretofore, $\Delta^7$-prostaglandins E have been totally unknown, and no process for their production has been known, either.

7-Hydroxyprostaglandins $E_1$, which could be the starting materials for the production of $\Delta^7$-prostaglandins E, were previously proposed by some of the present inventors (U.S. Pat. No. 4,315,032 and European Patent Application Publication No. 0019475 A3). But 7-hydroxyprostaglandins $E_2$ which can be useful as starting materials for the production of $\Delta^7$-prostaglandins E and their 5,6-dehydro derivatives have not been known at all in the past.

It is an object of this invention therefore to provide a process for producing prostaglandins $E_1$ with fewer steps than any chemical synthetic processes known heretofore.

Another object of this invention is to provide a process for producing prostaglandins $E_1$ in higher yields than in any conventional known processes.

Still another object of this invention is to provide an industrially very advantageous process for producing prostaglandins $E_1$ using 7-hydroxyprostaglandins E as starting materials.

Yet another object of this invention is to provide a process for producing prostaglandins $E_1$ from 7-hydroxyprostaglandins E through novel $\Delta^7$-prostaglandins E.

An additional object of this invention is to provide novel 7-hydroxyprostaglandins $E_2$ and their 5,6-dehydro derivatives which are useful as the starting materials in the above process of this invention or by themselves have useful pharmacological activities.

A further object of this invention is to provide novel $\Delta^7$-prostaglandins E which are useful as intermediates or starting materials for the aforesaid process of this invention for producing prostaglandins $E_1$, and by themselves have useful pharmacological activities.

Still other objects and advantages of this invention will become apparent from the following description.

These objects and advantages are first achieved by a process for producing prostaglandins $E_1$ represented by the following formula

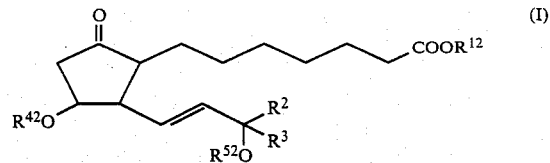 (I)

wherein $R^{12}$ represents a hydrogen atom, an alkyl group having 1 to 10 carbon atoms, or a tri($C_{1-7}$ hydrocarbon)-silyl group, $R^2$ represents an alkyl group having 1 to 10 carbon atoms which may be substituted, or a 5- or 6-membered cycloalkyl group which may be substituted, and $R_{42}$ and $R^{52}$ are identical or different and each represents a hydrogen atom or a protective group for the hydroxyl group, which comprises reacting a 7-hydroxyprostaglandin E represented by the following formula

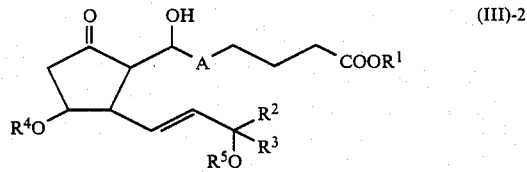 (III)-2 wherein $R^1$ represents a hydrogen atom, an alkyl group having 1 to 10 carbon atoms, or a tri($C_{1-7}$ hydrocarbon)-silyl group, $R^2$ and $R^3$ are as defined, $R^4$ and $R^5$ are identical or different and each represents a protective group for the hydroxyl group, and A represents —$CH_2CH_2$—, —CH=CH—, or —C≡C—, with a reactive derivative of an organic sulfonic acid in the presence of a basic compound to form the corresponding 7-organic sulfonyloxyprostaglandin E, treating the resulting 7-organosulfonyloxyprostaglandin E, after or without isolation, in the presence of a basic compound, then as required, eliminating the protective groups for the hydroxyl groups, and/or converting the group —$COOR^1$ in which $R^1$ is other than hydrogen to a carboxyl group, by hydrolysis to form a $\Delta^7$-prostaglandin E represented by the following formula

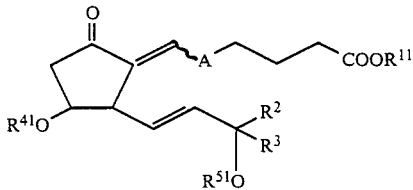

wherein $R^{11}$ represents a hydrogen atom, an alkyl group having 1 to 10 carbon atoms, or a tri($C_{1-7}$ hydrocarbon)-silyl group, $R^2$, $R^3$ and A are as defined, and $R^{41}$ and $R^{51}$ represent a hydrogen atom or a protective group for the hydroxyl group, thereafter selectively reducing the carbon-carbon unsaturated bond existing on the α-chain, and as required, eliminating the protective groups for the hydroxyl groups and/or converting the group —COOR$^{11}$ in which $R^{11}$ is other than hydrogen to a carboxyl group by hydrolysis.

It is understood that the 7-hydroxyprostaglandins E of formula (III)-2 used as the starting material in the process of this invention, according to the definition of A in formula (III)-2, include 7-hydroxyprostaglandins $E_2$ and their 5,6-dehydro derivatives of the following formula

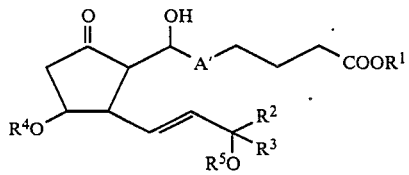

wherein $R^1$, $R^2$, $R^3$, $R^4$ and $R^5$ are as defined, and A' represents the group —CH=CH— or —C≡C—, and 7-hydroxyprostaglandins $E_1$ of the following formula

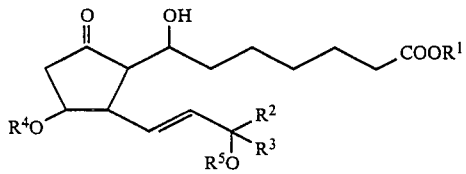

wherein $R^1$, $R^2$, $R^3$, $R^4$ and $R^5$ are as defined above.

The 7-hydroxyprostaglandins $E_2$ and their 5,6-dehydro derivatives of formula (III)'-2 are novel compounds and have been provided for the first time by the present inventors. These compounds of formula (III)'-2 are useful as the starting material in the process of this invention. Moreover, their parent compounds in which the hydroxyl groups at the 11- and 15-positions are free are novel compounds having by themselves excellent pharmacological activities, as will be shown hereinafter by Examples.

The 7-hydroxyprostaglandins $E_1$ of general formula (III)''-2 are known.

Like the 7-hydroxyprostaglandins $E_1$ represented by general formula (III)'-2, the novel 7-hydroxyprostaglandins $E_2$ or the 5,6-dehydro derivatives thereof represented by formula (III)'-2 can be produced by a process comprising reacting the corresponding cyclopent-2-en-1-ones with the corresponding organolithium compounds in the presence of cuprous salts in accordance with the method described in the specification of U.S. Pat. No. 4,315,032, and reacting the resulting β-substituted enolates with the corresponding aldehydes. U.S. Pat. No. 4,315,032 is hereby incorporated by reference.

Compounds of formula (III)'-2 in which A' is —CH=CH— can be produced by reducing compounds of formula (III)'-2 in which A' is —C≡C— produced as above.

This reduction is a reaction of catalytically reducing the triple bond (—C≡C—) to a double bond (—CH=CH—), and is carried out in a customary manner by using a Lindlar catalyst or Pd on $CaCO_3$ and quinoline.

In formula (III)-2 [including (III)'-2 and (III)''-2], $R^1$ represents a hydrogen atom, an alkyl group having 1 to 10 carbon atom, or a tri($C_{1-7}$ hydrocarbon)silyl group. Examples of the alkyl group having 1 to 10 carbon atoms are linear or branched $C_1$–$C_{10}$ alkyl groups such as methyl, ethyl, n-propyl, iso-propyl, n-butyl, sec-butyl, tert-butyl, n-pentyl, n-hexyl, n-heptyl, n-octyl, n-nonyl and n-decyl groups.

In the tri($C_{1-7}$ hydrocarbon)silyl group, the hydrocarbon moiety with 1 to 7 carbon atoms may include linear or branched alkyl groups such as methyl, ethyl, n-propyl, n-butyl, tert-butyl, n-pentyl, n-hexyl and n-heptyl groups, and aryl or aralkyl groups such as phenyl, tolyl and benzyl groups. Examples of the tri($C_{1-7}$ hydrocarbon)silyl group are tri($C_1$–$C_4$ alkyl)silyl groups such as trimethylsilyl triethylsilyl and tert-butyldimethylsilyl groups, diphenyl ($C_1$–$C_4$ alkyl)silyl groups such as a tert-butyldiphenylsilyl group, and a tribenzylsilyl group.

$R^2$ represents an alkyl group having 1 to 10 carbon atoms which may be substituted, or a 5- or 6-membered cycloalkyl group which may be substituted. Examples of the alkyl group having 1 to 10 carbon atoms include those exemplified hereinabove for $R^1$ and also include 2-hexyl and 2-methylhexyl groups. Of these, n-pentyl, n-hexyl, 2-hexyl and 2-methylhexyl groups are preferred. Examples of the 5- or 6-membered cycloalkyl group are cyclopentyl and cyclohexyl groups. Such a $C_1$–$C_{10}$ alkyl group or 5- or 6-membered cycloalkyl group may be substituted by a lower alkyl group such as methyl or ethyl (excepting $R^2$ being the $C_{1-10}$ alkyl group), a lower alkoxy group such as methoxy or ethoxy, a cycloalkyl group such as cyclopentyl or cyclohexyl, and such a substituent as ethenyl phenyl, phenoxy, trifluorophenyl or trifluoromethyl.

$R^3$ is a hydrogen atom or a methyl group.

$R^4$ and $R^5$ are identical or different, and each represents a protective group for the hydroxyl group. Examples of the protective group are tri($C_{1-7}$ hydrocarbon)silyl groups, or groups capable of forming an acetal linkage with the oxygen atom of the hydroxyl group. Examples of the tri($C_{1-7}$ hydrocarbon)silyl group may be the same as those exemplified hereinabove with regard to $R^1$. Examples of the groups capable of forming an acetal linkage together with the oxygen atom of the hydroxyl group include methoxyethyl, 1-ethoxyethyl, 2-methoxy-2-propyl, 2-ethoxy-2-propyl, (2-methoxyethoxy) methyl, benzyloxymethyl, 2-tetrahydropyranyl, 2-tetrahydrofuranyl, and 6,6-dimethyl-3-oxa-2-oxobicyclo[3.1.0.]hex-4-yl groups. Of these, the tert-butyldimethylsilyl, 1-ethoxyethyl, 2-methoxy-2-propyl, (2-methoxyethoxy)methyl, and 2-tetrahydropyranyl groups are preferred.

A represents the group —CH$_2$CH$_2$—, —CH=CH— or —C≡C—.

The 7-hydroxyprostaglandins E represented by the above formula (III)-2 correspond to compounds resulting from the protection of the hydroxyl groups at the 11- and 15-positions in the 7-hydroxyprostaglandins E (parent compounds) in which the hydroxyl groups at the 11- and 15-positions are free and which are represented by the following formula

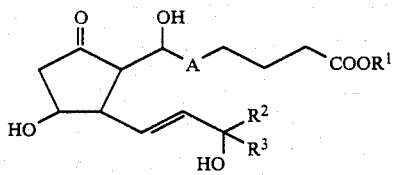

(III)-1 wherein R$^1$, R$^2$, R$^3$ and A are as defined hereinabove.

Accordingly, the compounds of formula (III)-2 are compounds resulting from the protection of the hydroxyl groups at the 11- and 15-positions of the parent compounds exemplified below by protective groups (R$^4$, R$^5$).

(300) 7-Hydroxy PGE$_1$,
(301) 7-Hydroxy-16-methyl PGE$_1$,
(302) 7-Hydroxy-16,16-dimethyl PGE$_1$,
(303) 7-Hydroxy-20-methyl PGE$_1$,
(304) 7-Hydroxy-17,20-dimethyl PGE$_1$,
(306) 7-Hydroxy-16,17,18,19,20-pentanor-15-cyclopentyl PGE$_1$,
(308) 7-Hydroxy-16,17,18,19,20-pentanor-15-cyclohexyl PGE$_1$,
(310) 7-Hydroxy-15-methyl PGE$_1$,
(312) 7-Hydroxy-17,17,20-trimethyl PGE$_1$,
(314) 7-Hydroxy-17,18,19,20-tetranor-16-cyclohexyl PGE$_1$, (The above compounds are examples of compounds in which the hydroxyl groups at the 11- and 15-positions are free. From these examples, specific examples of the compounds of general formula (III)'-2 will be understood.)

(320) 7-Hydroxy PGE$_2$,
(321) 7-Hydroxy-16-methyl PGE$_2$,
(322) 7-Hydroxy-16,16-dimethyl PGE$_2$,
(323) 7-Hydroxy-20-methyl PGE$_2$,
(324) 7-Hydroxy-17,20-dimethyl PGE$_2$,
(326) 7-Hydroxy-16,17,18,19,20-pentanor-15-cyclopentyl PGE$_2$,
(328) 7-Hydroxy-16,17,18,19,20-pentanor-15-cyclohexyl PGE$_2$,
(330) 7-Hydroxy-15-methyl PGE$_2$,
(332) 7-Hydroxy-17,17,20-trimethyl PGE$_2$,
(334) 7-Hydroxy-17,18,19,20-tetranor-16-cyclohexyl PGE$_2$,
(336) 7-Hydroxy-17,18,19,20-tetranor-16-phenoxy-PGE$_2$,
(340) 7-Hydroxy-5,6-dehydro-PGE$_2$,
(341) 7-Hydroxy-5,6-dehydro-16-methyl PGE$_2$,
(342) 7-Hydroxy-5,6-dehydro-16,16-dimethyl PGE$_2$,
(343) 7-Hydroxy-5,6-dehydro-20-methyl PGE$_2$,
(344) 7-Hydroxy-5,6-dehydro-17,20-dimethyl PGE$_2$,
(346) 7-Hydroxy-5,6-dehydro-16,17,18,19,20-pentanor-15-cyclopentyl PGE$_2$,
(348) 7-Hydroxy-5,6-dehydro-16,17,18,19,20-pentanor-15-cyclohexyl PGE$_2$,
(350) 7-Hydroxy-5,6-dehydro-15-methyl PGE$_2$,
(352) 7-Hydroxy-5,6-dehydro-17,17,20-trimethyl PGE$_2$,
(354) 7-Hydroxy-5,6-dehydro-18-oxa PGE$_2$,
(356) 7-Hydroxy-5,6-dehydro-17,18,19,20-tetranor-16-cyclopentyl PGE$_2$.

(The above are examples of compounds in which the hydroxyl groups at the 11- and 15-positions are free. From these examples, specific examples of compounds included within the formula (III)'-2 will be understood.)

The above-exemplified compounds have a free carboxyl group, but those skilled in the art will be able to easily understand specific examples of the corresponding compounds in which the carboxyl group is in the form of an ester.

According to the process of this invention, the 7-hydroxy PGE of formula (III)-2 is first reacted with a reactive derivative of an organic sulfonic acid in the presence of a basic compound to give the corresponding 7-organic sulfonyloxy PGE.

Preferred reactive derivatives of an organic sulfonic acid are organic sulfonic acid halides and organic sulfonic acid anhydrides.

Examples of suitable organic sulfonic acid halides are compounds of the following formula

(IV)

wherein R$^6$ represents an alkyl group having 1 to 4 carbon atoms which may be substituted by a halogen atom, a phenyl group which may be substituted, or a phenyl (C$_{1-2}$ alkyl) group which may be substituted, and X represents a halogen atom.

R$^6$ in formula (IV) is a C$_1$–C$_4$ alkyl group such as methyl, ethyl, propyl or butyl which may be substituted by a halogen atom such as fluorine, chlorine or bromine; a phenyl group which may be substituted; or a phenyl(C$_{1-2}$ alkyl) group which may be substituted such as benzyl or phenethyl. Specific examples of R$^6$ include alkyl groups having 1 to 4 carbon atoms which may be substituted by a halogen atom, such as methyl, ethyl, n-propyl, iso-propyl, n-butyl, tert-butyl, chloromethyl, dichloromethyl, trifluoromethyl and nonafluorobutyl groups; and a phenyl, benzyl, α-phenethyl or β-phenethyl group which may be substituted by a substituent selected from the class consisting of halogen atoms; C$_2$–C$_7$ acyloxy groups such as acetoxy, propionyloxy or benzoyloxy; C$_1$–C$_4$ alkyl groups which may be substituted by a halogen atom, C$_1$–C$_4$ alkoxy groups which may be substituted by a halogen atom, such as methoxy, ethoxy, chloromethoxy and trifluoromethoxy; a nitro group; a nitrile group; a carboxyl group; and alkoxycarbonyl groups with the alkoxy moiety having 1 to 6 carbon atoms, such as ethoxycarbonyl and methoxycarbonyl.

X is a halogen atom such as fluorine, chlorine, bromine or iodine. Chlorine and bromine are preferred, and chlorine is especially preferred.

Examples of the organic sulfonic acid halides include methanesulfonyl chloride, ethanesulfonyl bromide, n-butanesulfonyl chloride, tert-butanesulfonyl chloride, trifluoromethanesulfonyl chloride, nonafluorobutanesulfonyl chloride, benzenesulfonyl chloride, p-toluenesulfonyl chloride, 4-bromobenzenesulfonyl chloride, pentafluorobenzenesulfonyl chloride, 4-chloro-3-nitrobenzenesulfonyl chloride, 2,3,4-trichlorobenzenesulfonyl chloride, and 2-phenylethanesulfonyl chloride. Of these, methanesulfonyl chloride, trifluoromethanesulfonyl chloride, benzenesulfonyl chloride, and p-toluenesulfonyl chloride are preferred.

Examples of suitable organic sulfonyl acid anhydrides are compounds of the following formula

$$R^7-SO_2-O-SO_2-R^8 \quad (V)$$

wherein $R^7$ and $R^8$ are identical or different, and each represents a $C_1$-$C_4$ alkyl group which may be substituted by a halogen atom, a phenyl group which may be substituted, or a phenyl ($C_{1-2}$ alkyl) group which may be substituted.

Specific examples of $R^7$ and $R^8$ in formula (V) are the same as $R^6$ in formula (IV).

Specific examples of the organic sulfonic acid anhydride are methanesulfonic anhydride, ethanesulfonic anhydride, trifluoromethanesulfonic anhydride, nonafluorobutanesulfonic anhydride, benzenesulfonic anhydride, p-toluenesulfonic anhydride, trifluoromethanesulfonicbenzenesulfonic mixed anhydride, trifluoromethanesulfonic-p-toluenesulfonic mixed anhydride, and trifluoromethanesulfonic-4-nitrobenzenesulfonic mixed anhydride. Of these, methanesulfonic anhydride, trifluoromethanesulfonic anhydride and p-toluenesulfonic anhydride are preferred.

As the basic compound, organic amines, especially tertiary organic amines, are preferably used.

Examples of the organic amines include trimethylamine, triethylamine, isopropyldimethylamine, diisopropylcyclohexylamine, diisopropylethylamine, pyridine, 2,6-lutidine, 2,4,6-collidine, 4-(N,N-dimethyl)aminopyridine, 1,5-diazabicyclo[4.3.0.]non-5-ene, and 1,4-diazabicyclo[2.2.2]octane. Of these, triethylamine, pyridine, 2,6-lutidine, and 4-(N,N-dimethyl)aminopyridine are preferred.

The reaction is carried out usually in an aprotic inert organic solvent. Examples of the solvent include halogenated hydrocarbons such as dichloromethane, chloroform, carbon tetrachloride and 1,2-dichloroethane; ethers such as ethyl ether, tetrahydrofuran and dioxane; aromatic hydrocarbons such as benzene, toluene and xylene; aliphatic hydrocarbons such as hexane, pentane and cyclohexane; esters such as ethyl acetate; dimethylformamide; dimethyl sulfoxide; and hexamethyl phosphoramide. Of these, the halogenated hydrocarbons are preferred.

The above reaction is between the hydroxyl group at the 7-position of the 7-hydroxy PGE of formula (III)-2 and the reactive derivative of the organic sulfonic acid, and therefore, stoichiometrically, the two compounds react in equimolar proportions. The reaction proceeds, however, even when one of the starting compounds is used in an amount stoichiometrically less than the other. Hence, the use of these materials in such proportions may be permissible. In practice, about 1 to about 10 moles of the reactive derivative of the organic sulfonic acid is used per mole of the 7-hydroxy PGE of general formula (III)-2. Generally, when the rate of the reaction is slow, the reactive derivative of the organic sulfonic acid is used in excess.

The basic compound is used in an amount of at least about 1 mole, preferably at least 2 moles, per mole of the reactive derivative of the organic sulfonic acid. The basic compound may be used in excess, for example in such a large excess as to serve as a reaction solvent.

The reaction is carried out usually at 0° to 100° C., preferably 0° to 50° C., especially preferably 10° to 30° C. The reaction comes to an end usually in 0.5 to 10 hours. The progress of the reaction can be confirmed by monitering the disappearance of the starting compounds by, for example, thin-layer chromatography.

Thus, according to the aforesaid first reaction, there is formed a 7-organic sulfonyloxy PGE resulting from the conversion of the hydroxyl group at the 7-position of the 7-hydroxy PGE of formula (III)-2 into an organic sulfonyloxy group. In other words, the 7-organic sulfonyloxy PGE compounds have a partial structure formula

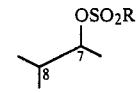

wherein R is the same as $R^6$ when the organic sulfonyl halide of formula (IV) is used, and as $R^7$ or $R^8$ when the organic sulfonic acid anhydride of formula (V) is used.

According to this invention, the 7-organic sulfonyloxy PGE is then treated with a basic compound. As a result, the 7-organic sulfonyloxy PGE releases the corresponding organic sulfonic acid ($RSO_3H$) and is thus converted to a $\Delta^7$-PGE in which a double bond is formed between the carbon atom at the 7-position and the carbon atom at the 8-position.

This second reaction can generally be carried out at the same temperature using the same basic compound as in the first reaction.

The first and second reactions in the process of this invention may be carried out such that after the 7-organic sulfonyloxy PGE formed in the first reaction is isolated, the second reaction is performed; or that without isolating the 7-organic sulfonyloxy PGE formed in the first reaction, the second reaction is performed in the same reaction system or after optionally adding a fresh supply of the basic compound to the reaction system.

Depending upon various factors such as the type of the basic compound used, the reaction temperature or the type of the reactive derivative of the organic sulfonic acid (therefore, the type of the 7-organic sulfonyloxy PGE formed), it is determined whether or not the second reaction of converting the 7-organic sulfonyloxy PGE formed by the first reaction proceeds in the same reaction system. For example, when a compound having relatively weak basicity is used as the basic compound, the 7-organic sulfonyloxy PGE can be accumulated in the reaction system without substantial proceeding of the second reaction. In this case, the 7-organic sulfonyloxy PGE may be isolated from the reaction system after the first reaction and subjected to the second reaction. Of course, the second reaction can also be carried out without isolating the 7-organic sulfonyloxy PGE formed in the first reaction system, by, for example, heating the reaction system to a temperature higher than the reaction temperature of the first reaction, or adding a fresh supply of a compound having stronger basicity than the basic compound used in the first reaction. On the other hand, when a compound having strong basicity is used in the first reaction, the 7-organic sulfonyloxy PGE formed by the first reaction can be converted to a $\Delta^7$-PGE in the same reaction system by the concurrent proceeding of the second reaction with the first reaction.

Hence, the aforesaid process which comprises reacting the 7-hydroxyprostaglandin E with the reactive derivative of the organic sulfonic acid in the presence of the basic compound and then treating the product with the basic compound gives the corresponding $\Delta^7$-prostaglandin E having a double bond between the carbon atom at the 7-position and the carbon atom at the 8-position.

It is believed that when a 7-hydroxyprostaglandin E of general formula in which $R^1$ is a hydrogen is used as the starting material, the resulting $\Delta^7$-PGE is in the form of a mixed acid anhydride formed between the carboxyl group and the organic sulfonic acid. When other 7-hydroxyprostaglandins E of general formula (III)-2 are used, the products generally retain $R^1$, $R^4$ and $R^5$ existing in general formula (III)-2.

According to this invention, the resulting $\Delta^7$-PGE is generally separated from the reaction system, and then as required, the protective groups ($R^4$, $R^5$) for the hydroxyl groups are eliminated (deprotection) and/or when $R^1$ is other than hydrogen atom, the group —COOR$^1$ is converted to a carboxyl group by hydrolysis.

Elimination of the protective groups for the hydroxyl groups can be carried out as follows: When the protective groups are groups forming acetal linkages with oxygen atoms, the deprotection may be conveniently carried out in a reaction solvent such as water, tetrahydrofuran, ethyl ether, dioxane, acetone or acetonitrile using acetic acid, pyridinium p-toluenesulfonate, a cation exchange resin, etc. as a catalyst. The reaction is carried out usually at $-20°$ C. to $+80°$ C. for a period of 10 minutes to 3 days. When the protective groups are tri($C_{1-7}$ hydrocarbon)silyl groups, the deprotection may be carried out at the same temperature for the same period of time as above in the above-exemplified reaction solvent in the presence of acetic acid, hydrogen fluoride, tetrabutyl ammonium fluoride, or cesium fluoride, preferably acetic acid and hydrogen fluoride.

Hydrolysis of the ester group (—COOR$^1$ wherein $R^1$ is an alkyl group having 1 to 10 carbon atoms) may be carried out, for example, by treating the $\Delta^7$-PGE, with or without prior deprotection, with an enzyme such as lipase in water or a water-containing solvent at a temperature in the range of 0° C. to 40° C. for a period of 10 minutes to 24 hours.

The ester group in which $R^1$ is a tri($C_{1-7}$ hydrocarbon)silyl group can be easily converted to a carboxyl group, for example by treatment in an acidic or basic aqueous medium at a temperature of 0° C. to $+30°$ C. When the resulting $\Delta^7$-PGE is in the form of a mixed acid anhydride with the organic sulfonic acid, conversion to a carboxyl group can be easily effected simply by contacting the mixed acid anhydride with water (for example, when treating it with water in separating it from the reaction system).

According to the above reaction, therefore, there is formed a $\Delta^7$-prostaglandin E of the following formula

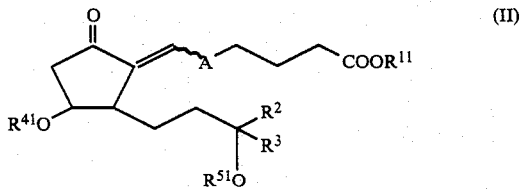

(II)

wherein $R^{11}$ represents a hydrogen atom, an alkyl group having 1 to 10 carbon atoms, or a tri($C_{1-7}$ hydrocarbon)-silyl group, $R^2$, $R^3$ and A are as defined hereinabove, and $R^{41}$ and $R^{51}$ are identical or different and each represents a hydrogen atom or a protective group for the hydroxyl group.

$\Delta^7$-Prostaglandins E of formula (II) are novel compounds and constitute part of the present invention.

The definitions of $R^2$, $R^3$ and A in formula (II) are the same as in formula (I), and examples of these include those compounds already exemplified hereinabove. $R^{11}$, $R^{41}$ and $R^{51}$ in formula (II) correspond to $R^1$, $R^4$ and $R^5$ in formula (I), and examples of these include those compounds already exemplified hereinabove with regard to $R^1$, $R^4$ and $R^5$ in formula (I).

The symbol ∾ connecting the carbon atom at the 7-position and A (the carbon atom at the 6-position) in formula (II) means that with regard to the double bond between the carbon atoms at the 7- and 8-positions, the bond between the carbon atom at the 7-position and the carbon atom at the 6-position may be cis (Z-form) or trans (E-form) or mixed cis and trans to the bond between the carbon atom at the 8-position and the carbon atom at the 9-position (the carbon atom of the carbonyl group).

Examples of the novel $\Delta^7$-prostaglandins E of formula (II) are given below.
(200) $\Delta^7$-PGE$_1$,
(202) $\Delta^7$-16-methyl PGE$_1$,
(204) $\Delta^7$-16,16-dimethyl PGE$_1$,
(206) $\Delta^7$-20-methyl PGE$_1$,
(208) $\Delta^7$-17,20-dimethyl PGE$_1$,
(210) $\Delta^7$-16,17,18,19,20-pentanor-15-cyclopentyl PGE$_1$,
(212) $\Delta^7$-16,17,18,19,20-pentanor-15-cyclohexyl PGE$_1$,
(214) $\Delta^7$-15-methyl PGE$_1$,
(216) $\Delta^7$-17,17,20-trimethyl PGE$_1$,
(218) $\Delta^7$-17,18,19,20-tetranor-16-cyclohexyl PGE$_1$,
(230) $\Delta^7$-PGE$_2$,
(232) $\Delta^7$-16-methyl PGE$_2$,
(234) $\Delta^7$-16,16-dimethyl PGE$_2$,
(236) $\Delta^7$-20-methyl PGE$_2$,
(238) $\Delta^7$-17,20-dimethyl PGE$_2$,
(240) $\Delta^7$-16,17,18,19,20-pentanor-15-cyclopentyl PGE$_2$,
(242) $\Delta^7$-16,17,18,19,20-pentanor-15-cyclohexyl PGE$_2$,
(244) $\Delta^7$-15-methyl PGE$_2$,
(246) $\Delta^7$-17,17,20-trimethyl PGE$_2$,
(248) $\Delta^7$-17,18,19,20-tetranor-16-cyclohexyl PGE$_2$,
(260) $\Delta^7$-5,6-dehydro-PGE$_2$,
(262) $\Delta^7$-5,6-dehydro-16-methyl PGE$_2$,
(264) $\Delta^7$-5,6-dehydro-16,16-dimethyl PGE$_2$,
(266) $\Delta^7$-5,6-dehydro-20-methyl PGE$_2$,
(268) $\Delta^7$-5,6-dehydro-17,20-dimethyl PGE$_2$,
(270) $\Delta^7$-5,6-dehydro-16,17,18,19,20-pentanor-15-cyclopentyl PGE$_2$,
(272) $\Delta^7$-5,6-dehydro-16,17,18,19,20-pentanor-15-cyclohexyl PGE$_2$,
(274) $\Delta^7$-5,6-dehydro-15-methyl PGE$_2$,
(276) $\Delta^7$-5,6-dehydro-17,17,20-trimethyl PGE$_2$,
(278) $\Delta^7$-5,6-dehydro-18-oxa PGE$_2$, and
(280) $\Delta^7$-5,6-dehydro-17,18,19,20-tetranor-16-cyclopentyl PGE$_2$.

The above compounds are those in which the carboxyl group and the hydroxyl groups are free. Those skilled in the art will easily understand specific examples of the corresponding compounds in which the carboxyl group forms an ester and/or the hydroxyl groups are protected.

The $\Delta^7$-PGE compounds of formula (II) are important intermediates for the production of PGE$_1$ compounds from 7-hydroxy PGE compounds in accordance with the process of this invention, and also have excellent pharmacological activities by themselves as will be shown later by Examples.

According to the process of this invention, the $\Delta^7$-PGE is then subjected to selective reduction of the carbon-carbon unsaturated bond existing on its $\alpha$-chain. The carbon-carbon unsaturated bond existing on the $\alpha$-chain means a carbon-carbon unsaturated bond existing on the $\alpha$-chain in accordance with the nomenclature customarily used in the field of prostaglandin technology. In formula (II), the $\alpha$-chain is a chain bonded to the 2-position of the cyclopentanone ring (the carbonyl group is taken as the 1-position). It is to be understood therefore that the carbon-carbon double bond existing on this chain is the double bond between the 7- and 8-position, and if present, the double bond or triple bond between the 5- and 6-positions.

It is to be understood that the term "selective reduction" or the corresponding verbal expression means that the carbon-carbon unsaturated bond on the $\alpha$-chain is reduced, while the carbon-carbon double bond on the $\beta$-chain, i.e. the double bond at the 13-position, remains unreduced.

According to the process of this invention, the selective reduction of the $\Delta^7$-PGE of formula (II) is carried out preferably by using metallic zinc or a reducing agent containing metallic zinc, or by catalytic reduction in the presence of a Raney nickel catalyst. When metallic zinc or the reducing agent containing metallic zinc is used, the reaction proceeds advantageously in the presence of a carboxylic acid such as glacial acetic acid, propionic acid or trichloroacetic acid. The metallic zinc or the reducing agent containing it is used in an amount of about 1 to about 100 moles, preferably about 5 to about 50 moles, as metallic zinc, for each of the carbon-carbon unsaturated bonds to be reduced (the triple bond is counted as two unsaturated bonds). The carboxylic acid is used in an amount of 1 to 20 moles, preferably 2 to 10 moles, per mole of metallic zinc in the reducing agent.

The reaction is desirably carried out in the presence of a solvent, for example alcohols such as methanol, ethanol, isopropanol or butanol, acetic acid, dimethoxyethane, dimethylformamide, dimethyl sulfoxide, or mixtures of these. The alcohols, especially isopropanol, are preferred as the solvent. The catalytic reduction with Raney nickel, on the other hand, is carried out in an atmosphere of hydrogen. The Raney nickel catalyst is used in an amount of 0.01 to 0.2 part by weight, preferably 0.05 to 0.1 part by weight, per part by weight of the $\Delta^7$-PGE. To cause the reaction to proceed smoothly, a solvent is preferably used. Examples of the solvent are alcohols such as methanol, ethanol and butanol, ethers such as dimethoxyethane and tetrahydrofuran, dimethylformamide, and mixtures of these. Methanol is preferred.

The selective reduction gives the corresponding PGE$_1$ having no carbon-carbon unsaturated bond on the $\alpha$-chain.

Furthermore, in the aforesaid selective reduction, the double bond between the 7- and 8-positions is stereoselectively reduced so that a product in which the $\alpha$-chain and $\beta$-chain are trans to each other is formed in a major proportion. Accordingly, if the above selective reduction is carried out by using natural type $\Delta^7$-PGE compounds of formula (II)-a$_1$ mentioned below (the $\beta$-chain is of $\beta$-configuration and the group —OR$^{41}$ is of $\alpha$-configuration) which are embraced by formula (II), the corresponding PGE$_1$ compounds of the natural type can be selectively obtained.

As required, the resulting PGE$_1$ is separated from the reaction system, and in the same way as described hereinabove, the protective groups for the hydroxyl groups are eliminated, and/or the group —COOR$^{11}$ in which R$^{11}$ is other than hydrogen is converted to a carboxyl group by hydrolysis.

PGE$_1$ may be isolated or purified from the reaction mixture after the reducing reaction or after the subsequent deprotection and/or hydrolysis in a customary manner, for example by extraction, washing with water, drying and chromatography.

Thus, according to this invention, there is produced a prostaglandin E$_1$ expressed by the following formula (I)

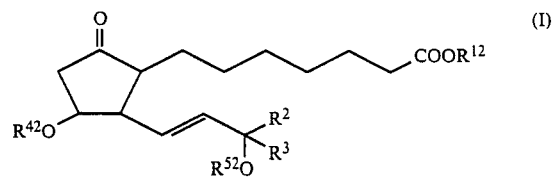

wherein R$^{12}$ represents a hydrogen atom, an alkyl group having 1 to 10 carbon atoms or a tri(C$_{1-7}$ hydrocarbon)-silyl group, R$^2$ and R$^3$ are as defined hereinabove, and R$^{42}$ and R$^{52}$ are identical or different and each represents a hydrogen atom or a protective group for the hydroxyl group.

The PGE$_1$ compounds of formula (I) are known compounds. In formula (I), R$^{12}$, R$^2$, R$^3$, R$^{42}$ and R$^{52}$ correspond respectively to R$^{11}$, R$^2$, R$^3$, R$^{41}$ and R$^{52}$ of formula (I). Accordingly, the same examples as above may be given to these groups.

Examples of the PGE$_1$ compounds of formula (I) are shown below.
(100) PGE$_1$,
(102) 16-methyl PGE$_1$,
(104) 16,16-dimethyl PGE$_1$,
(106) 20-methyl PGE$_1$,
(108) 17,20-dimethyl PGE$_1$,
(110) 16,17,18,19,20-pentanor-15-cyclopentyl PGE$_1$,
(112) 16,17,18,19,20-pentanor-15-cyclohexyl PGE$_1$,
(114) 15-methyl PGE$_1$,
(116) 17,17,20-trimethyl PGE$_1$,
(118) 18-oxa PGE$_1$,
(120) 17,18,19,20-tetranor-16-cyclopentyl PGE$_1$,
(122) 17,18,19,20-tetranor-16-cyclohexyl PGE$_1$.

It will be easy for those skilled in the art to understand specific examples of the corresponding compounds of the above PGE$_1$ compounds in which the carboxyl group forms an ester and/or the hydroxyl groups are protected.

It will be understood from the foregoing description that according to the process of this invention, prostaglandins E$_1$ can be produced industrially advantageously in high yields by fewer steps than any conventional known processes based on chemical synthesis.

As already stated, the present invention provides 7-hydroxyprostaglandins E and $\Delta^7$-prostaglandins E which are novel compounds useful as starting materials or intermediates for the process of this invention or as compounds which by themselves have excellent pharmacological activities.

The novel 7-hydroxyprostaglandins E provided by this invention are expressed by the following formula

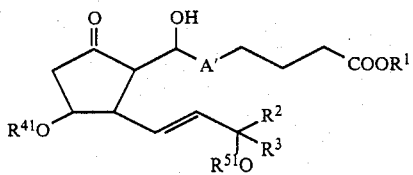

(III)′ wherein R[1] represents a hydrogen atom, an alkyl group having 1 to 10 carbon atoms, or a tri($C_{1-7}$ hydrocarbon)silyl group, R[2] represents an alkyl group having 1 to 10 carbon atoms which may be substituted or a 5- or 6-membered cycloalkyl group which may be substituted, R[3] represents a hydrogen atom or a methyl group, R[41] and R[51] are identical or different and each represents a protective group for the hydroxyl group, and A′ represents the group —CH=CH— or —C≡C—.

The PGE compounds expressed by formula (III)′ include natural-type 7-hydroxyprostaglandins $E_2$ and their 5,6-dehydro derivatives of the following formula

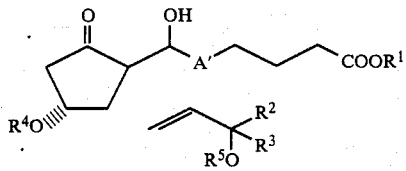

(III)′-a₁ wherein R[1], R[2], R[3], R[4], R[5] and A′ are as defined above,
and nonnatural-type 7-hydroxyprostaglandins $E_2$ and their 5,6-dehydro derivatives expressed by the following formula

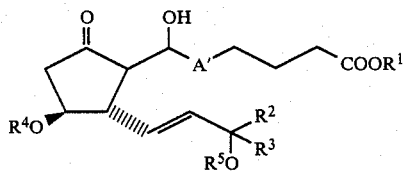

(III)′-a₂ wherein R[1], R[2], R[3], R[4], R[5] and A′ are as defined above.

The 7-hydroxy PGE compounds (7-hydroxy $PGE_2$ compounds and their 5,6-dehydro derivatives) expressed by formula (III)′ [including formulae (III)′-a₁ and (III)′-a₂] consist of 7-hydroxy PGE compounds having protected hydroxyl groups represented by formula (III)′-2 and 7-hydroxy PGE compounds with free hydroxyl groups represented by the following formula

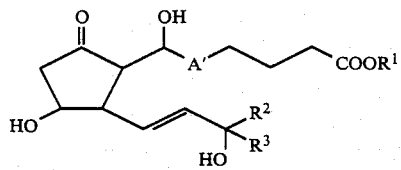

(III)′-1 wherein R[1], R[2], R[3] and A′ are as defined.

Specific examples of the 7-hydroxy PGE compounds of formula (III)′-1 wherein R[1] is a hydrogen atom are given hereinabove by compound numbers (320) to (356). It will be easy for those skilled in the art to understand from the above examples (320) to (356) specific examples of the compounds of formula (III)′ [including formulae (III)′-a₁, (III)′-a₂, (III)′-1 and (III)′-2].

The novel $\Delta^7$-prostaglandins E provided by this invention are expressed by formula (II) already given above.

The $\Delta^7$-PGE compounds expressed by formula (II) also include natural-type $\Delta^7$-PGE compounds of the formula

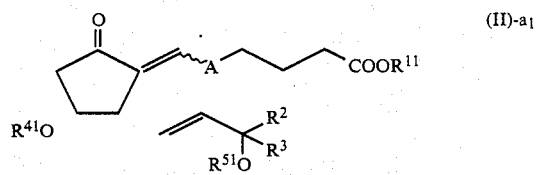

(II)-a₁ wherein R[11], R[2], R[3], R[41], R[51] and A are as defined hereinabove,
and nonnatural-type $\Delta^7$-PGE compounds of the formula

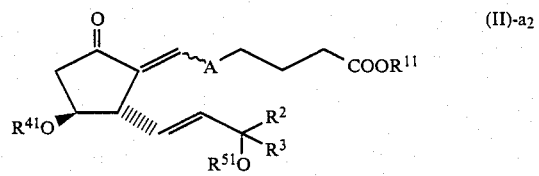

(II)-a₂ wherein R[11], R[2], R[3], R[41], R[51] and A are as defined hereinabove

The $\Delta^7$-PGE compounds of formula (II) [including formulae (II)-a₁ and (II)-a₂] consist of $\Delta^7$-PGE compounds with the hydroxyl groups being free represented by the following formula

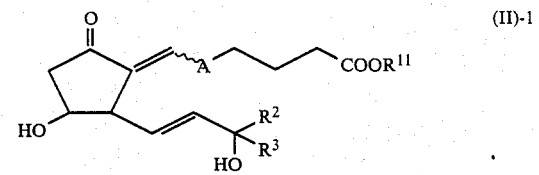

(II)-1 wherein R[11], R[2], R[3] and A are as defined hereinabove,
and $\Delta^7$-PGE compounds having protected hydroxyl groups represented by the following formula

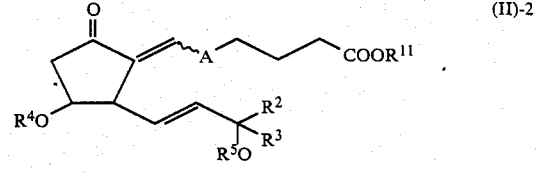

(II)-2 wherein R[11], R[2], R[3], R[4], R[5] and A are as defined hereinabove.

Among the $\Delta^7$-PGE compounds of formula (II) [including formulae (II)-a₁, (II)-a₂, (II)-1 and (II)-2], those in which R[2] is an alkyl group having 5 to 8 carbon atoms which may be substituted or a 5- or 6-membered cycloalkyl group which may be substituted are preferred, and those in which R[11] is a hydrogen atom, a methyl group or an ethyl group are likewise preferred.

$\Delta^7$-PGE compounds expressed by the following formula

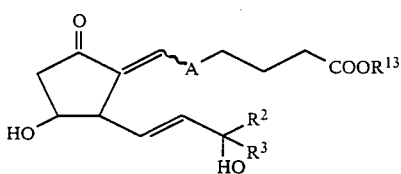

wherein $R^2$, $R^3$ and A are as defined above and $R^{13}$ is a hydrogen atom, a methyl group or an ethyl group, are especially preferred in this invention.

Specific examples of $\Delta^7$-PGE of formula (II)-1 in which $R^{11}$ is a hydrogen atom or $\Delta^7$-PGE of formula (II)-1' in which $R^{13}$ is a hydrogen atom are already given hereinabove by compound numbers (200) to (280). It will be easy for those skilled in the art to understand specific examples of compounds of formula (II) [including formulae (II)-$a_1$, (II)-$a_2$, (II)-1, and (II)-2] provided by this invention from the above examples (200) to (280).

The following Examples illustrate the present invention more specifically. Examples 54 and 55 show the pharmacological activities of novel 7-hydroxy PGE compounds and $\Delta^7$-PGE compounds provided by this invention.

Referential Example 1

Synthesis of 7-hydroxy-PGE$_1$ t-butyldimethylsilyl ester 11,15-bis-(t-butyldimethylsilyl) ether 810 mg (2.2 mmoles) of (1E, 3S)-3-t-butyldimethylsilyloxy-1-iodo-1-octene was dissolved in 10 ml of anhydrous ether, and the solution was cooled to $-78°$ C. 1.96 ml (4.4 mmoles) of a 2.24M pentane solution of t-butyl lithium was added, and the mixture was stirred at $-78°$ C. for 80 minutes to form an alkenyl lithium solution. Separately, 1.0 ml (4.6 mmoles) of hexamethylphosphoric triamide was added to 287 mg (2.2 mmoles) of 1-pentynyl copper (I) and the mixture was stirred at room temperature for 1 hour. To the resulting solution was added 10 ml of anhydrous ether and the solution was cooled to $-78°$ C. The resulting solution was added to the alkenyl lithium solution prepared as above, and the mixture was stirred at $-78°$ C. for 15 minutes. The reaction was carried out in an atmosphere of argon. To the resulting solution was added a solution cooled to $-78°$ C. of 425 mg (2.0 mmoles) of 4-t-butyldimethylsilyloxy-2-cyclopentenone in 10 ml of anhydrous ether. The mixture was stirred at $-78°$ C. for 10 minutes and then at $-50°$ C. for 10 minutes. A solution cooled to $-50°$ C. of 620 mg (2.4 mmoles) of t-butyldimethylsilyl 7-oxo-heptanoate in 10 ml of anhydrous ether was added to the resulting solution, and the mixture was stirred at $-50°$ C. to $-40°$ C. for 1.5 hours. The reaction mixture was poured into an acetic acid/sodium acetate buffer adjusted to pH 4, and thereafter extracted with hexane. The extract was dried over anhydrous magnesium sulfate, filtered and concentrated to give 7-hydroxy-PGE$_1$ t-butyldimethylsilyl ester 11,15-bis-(t-butyldimethylsilyl)ether as an oil (850 mg).

Rf=0.39 (hexane:acetone=4:1).

Referential Example 2

Synthesis of 7-hydroxy PGE$_1$ 11,15-bis-(t-butyldimethylsilyl)ether 850 mg of the oily 7-hydroxy-PGE$_1$ t-butyldimethylsilyl ester 11,15-bis-(t-butyldimethylsilyl)ether obtained in Referential Example 1 was dissolved in 30 ml of ether, and 50 ml of hydrochloric acid at a pH of 1 was added. The mixture was stirred for 20 minutes. The reaction mixture was extracted with ether. The etheric layer was washed with a saturated aqueous solution of sodium chloride, dried over anhydrous magnesium sulfate, filtered and concentrated. The residue was chromatographed on a silica gel column to give 524 mg (yield 44%) of 7-hydroxy-PGE$_1$ 11,15-bis-(t-butyldimethylsilyl)ether Rf=0.42 (hexane:acetone=2:1), IR (liquid film, cm$^{-1}$): 3450, 1726, 1708, 1252, 836.

NMR (CDCl$_3$, $\delta$ppm): 0–0.2 (m, 12H), 0.87 (s, 18H), 0.7–1.1 (m, 3H), 1.0–3.0 (m, 22H), 3.5–3.9 (m, 1H), 3.8–4.4 (m, 2H), 5.3–5.7 (m, 2H), 5.5–7.0 (m, 2H).

Referential Example 3

Synthesis of 7-hydroxy-PGE$_1$ methyl ester 11,15-bis-(t-butyldimethylsilyl)ether 1.16 g (3.15 mmoles) of (1E, 3S)-3-t-butyldimethylsilyloxy-1-iodo-1-octene was dissolved in 10 ml of dry ether, and the solution was cooled to $-78°$ C. 2.81 ml (6.3 mmoles) of a t-butyl lithium solution (2.24M) was added to the resulting solution, and the mixture was stirred at $-78°$ C. for 1.5 hours to form an alkenyl lithium. Separately, 1.43 ml (0.45 mmoles) of hexamethylphosphoric triamide was added to 411 mg (3.15 mmoles) of 1-pentynyl copper (I), and the mixture was stirred at room temperature for 1 hour. The resulting solution and 10 ml of dry ether were added to the alkenyl lithium solution prepared as above. The mixture was stirred at $-78°$ C. for 15 minutes, and a solution cooled to $-78°$ C. of 637 mg (3.0 mmoles) of 4-t-butyldimethylsiloxy-2-cyclopentenone in 10 ml of dry ether was added. The mixture was stirred for 30 minutes. A solution cooled to $-78°$ C. of 522 mg (3.3 mmoles) of methyl 7-oxoheptanoate in 10 ml of dry ether was added, and the mixture was stirred at $-78°$ C. for 5 minutes and at $-40°$ C. for 70 minutes. An acetate buffer having a pH of 4 (consisting of 82 ml of 0.2M acetic acid and 18 ml of 0.2M aqueous sodium acetate solution) and 50 ml of hexane were vigorously stirred, and the reaction mixture was poured into the stirred solution. The mixture was stirred for 5 minutes. The organic layer was washed three times with ammonium chloride-aqueous ammonia, three times further with an aqueous solution of ammonium chloride, and further with a saturated aqueous solution of sodium chloride. The organic layer was dried over anhydrous magnesium sulfate, filtered and concentrated. The residue was chromatographed on a silica gel column to separate the following three isomers.

Isomer 1 (7-hydroxy-PGE$_1$ methyl ester 11,15-bis-(t-butyldimethylsilyl)ether; 570 mg):

Rf=0.47 (hexane:ethyl acetate=3:1),

IR (CHCl$_3$ solution, cm$^{-1}$): 3450, 1728, 1253, 833.

NMR (CDCl$_3$, $\delta$ppm): 0–0.2 (m, 12H), 0.87 (s, 18H), 0.65–1.15 (m, 3H), 1.0–3.0 (m, 22H), 3.27 (d, 1H), 3.68 (s, 3H), 3.5–3.9 (m, 1H), 3.9–4.4 (m, 2H), 5.4–5.8 (m, 2H).

Isomer 2 (7-epimer of isomer 1; 45 mg):

Rf=0.43 (hexane:ethyl acetate=3:1).

IR (CHCl$_3$ solution, cm$^{-1}$): 3450, 1735, 1253, 908, 836.

NMR (CDCl₃, δppm): 0–0.2 (m, 12H), 0.87 (s, 18H), 0.65–1.15 (m, 3H), 1.0–3.2 (m, 23H), 3.26 (s, 3H), 3.7–4.4 (m, 3H), 5.4–5.8 (m, 2H).

Isomer 3:
Rf=0.46 (hexane:ethyl acetate=3:1),
IR (CHCl₃ solution, cm⁻¹): 3450, 1730, 1251, 903, 833).
NMR (CDCl₃, δppm): 0–0.2 (m, 12H), 0.87 (s, 18H), 0.65–1.15 (m, 3H), 1.0–3.2 (m, 23H), 3.26 (s, 3H), 3.7–4.6 (m, 3H), 5.4–5.8 (m, 2H).

Isomer 3 was believed to be a mixture of the 8-epimer of isomer 1 and the 8-epimer of isomer 2.

EXAMPLE 1

Synthesis of (7S) and (7R)-7-hydroxy-5,6-dehydro-PGE₁ methyl ester 11,15-bis-(t-butyldimethylsilyl)ethers:

1.88 g (5.10 mmoles) of 1-iodo-3-(t-butyldimethylsilyloxy)-trans-1-octene was taken into a 150 ml reaction tube, and the inside of the reaction tube was purged with argon. Dry ether (20 ml) was added, and the mixture was cooled to −78° C. To the solution was added 7.54 ml (10.4 mmoles) of a 1.38M pentane solution of t-butyl lithium, and the mixture was stirred for 2.5 hours. Separately, 971 mg (5.10 mmoles) of cuprous iodide was taken into a 30 ml test tube, and the inside of the flask was dried by heating under reduced pressure and then purged with argon. Dry ether (20 ml) and 2.54 ml (10.2 mmoles) of tributyl phosphine were added and the mixture was shaken to form a colorless clear solution. The solution was cooled to −78° C., and added to the vinyl lithium solution prepared as above. The test tube was washed by using 20 ml of dry ether.

To the resulting organic copper reagent solution was added dropwise over 15 minutes 30 ml of a solution of 1.06 g (5.00 mmoles) of 4-(t-butyldimethylsilyloxy)-2-cyclopentenone in ether. The mixture was further stirred for 5 minutes. The temperature was raised to −40° C., and the mixture was stirred for 15 minutes. Then, the solution was cooled to −78° C., and 20 ml of a solution of 848 mg (5.50 mmoles) of 6-carbomethoxy-2-hexynal in ether was added, followed by stirring for 5 minutes. The temperature was again raised to −40° C., and the mixture was stirred for 20 minutes. Then, 30 ml of a saturated aqueous solution of ammonium chloride was added, and the mixture was shaken vigorously to separate the ether layer. The aqueous layer was extracted with two 20 ml portions of ether. The etherial layers were combined and dried over anhydrous magnesium sulfate, and concentrated. The residue was chromatographed on a silica gel column (150 g) using hexane-ether (3:1) as an eluent to separate (7S) and (7R)-7-hydroxy-5,6-dehydro-PGE₂ methyl ester 11,15-bis-(t-butyldimethylsilyl)ethers [the total amount of (7S) and (7R) formed was 1.22 g; yield 39%].

(7S)-7-hydroxy-5,6-dehydro-PGE₂ methyl ester 11,15-bis-t-butyldimethylsilyl)ether:
Rf=0.23 (hexane:ether=1:1),
NMR (CDCl₃ δppm): 5.7–5.5 (m, 2H), 4.7–4.3 (br, 1H), 4.2–4.0 (m, 2H), 3.68 (s, 3H), 2.9–2.0 (m, 7H), 2.0–1.1 (m), 0.91 (s, 21H), 0.1–0.0 (m).
IR (neat, cm⁻¹): 3500, 1746.

(7R)-7-hydroxy-5,6-dehydro-PGE₂ methyl ester 11,15-bis-(t-butyldimethylsilyl)ether:
Rf=0.20 (hexane:ether=1:1)
NMR (CDCl₃, δppm): 5.7–5.5 (m, 2H), 4.8–4.3 (br, 1H), 4.2–4.0 (m, 2H), 3.69 (s, 3H), 3.0–2.0 (m, 7H), 2.0–1.1 (m), 0.92 (m, 21H), 0.10–0.0 (m).
IR (neat, cm⁻¹): 3494, 1748.
Mass (20 eV, m/e): 590 (M⁺−18).

EXAMPLE 2

Synthesis of 7-hydroxy-5,6-dehydro-PGE₂ methyl ester 26 mg of a mixture of the two isomers obtained in Example 1 was dissolved in a mixture of 0.3 ml acetic acid, 0.2 ml tetrahydrofuran (THF) and 0.2 ml water, and stirred at room temperature for 24 hours. Toluene was added, and the solvent was evaporated from the reaction solution under reduced pressure to give 12 mg (74%) of the desired 7-hydroxy-5,6-dehydro-PGE₂ methyl ester.

NMR (CDCl₃, δ ppm): 5.70 (2H, m), 4.3–4.8 (1H, m), 3.7–4.25 (2H, m), 3.65 (3H, s), 1.1–3.0 (21H), 3.9 (3H).
IR (CDCl₃ solution, cm⁻¹): 3230, 2250, 1730.
Mass (20 eV, m/e): 362 (M⁺−18).

EXAMPLES 3 to 7

Example 1 was followed to give the compounds shown in Table 1. Their spectral data are also shown in Table 1.

TABLE 1

| Example | Compound obtained | NMR (CDCl₃ δppm) | IR (cm⁻¹) |
|---|---|---|---|
| 3 | 7-Hydroxy-16,17,18,19,20-pentanor-15-cyclohexyl-5,6-dehydro-PGE₂ methyl ester 11,15-bis-(t-butyldimethylsilyl) ether | 0–0.2 (m, 12H), 0.89 (s, 18H), 1.1–2.9 (m, 22H), 3.68 (s, 3H), 4.0–4.8 (m, 3H), 5.4–5.8 (m, 2H). | 3495, 2230, 1745, 1255, 834, 772. |
| 4 | 7-Hydroxy-16,17,18,19,20-pentanor-15-cyclopentyl-5,6-dehydro-PGE₂ methyl ester 11,15-bis-(t-butyl-dimethylsilyl) ether | 0–0.2 (m,12H), 0.88 (s, 18H), 1.1–2.9 (m, 20H), 3.69 (s, 3H), 4.0–4.8 (m, 3H), 5.4–5.8 (m, 2H). | 3490, 2225, 1743, 1254, 833, 771. |
| 5 | (17S)-7-Hydroxy-5,6-dehydro-17,20-dimethyl PGE₂ methyl ester 11,15-bis-(t-butyl-methylsilyl) ether | 0–0.2 (m, 12H), 0.88 (s, 18H), 0.7–1.1 (m, 6H), 1.1–2.9 (m, 20H), 3.68 (s, 3H), 4.0–4.8 (m, 3H), 5.4–5.8 (m, 2H). | 3480, 2230, 1744, 1253, 833, 772. |
| 6 | (17R)-7-Hydroxy-5,6-dehydro-7,20-dimethyl PGE₂ methyl ester 11,15-bis-(t-butyl-dimethylsilyl) ether | 0–0.2 (m, 12H), 0.88 (s, 18H), 0.7–1.1 (m, 6H), 1.1–3.0 (m, 20H), 3.69 (s, 3H), | 3500, 2220, 1743, 1253, 832, 772. |

TABLE 1-continued

| Example | Compound obtained | NMR (CDCl$_3$ δppm) | IR (cm$^{-1}$) |
|---|---|---|---|
| 7 | (5E)-7-hydroxy-5,6-dehydro-PGE$_1$ methyl ester 11,15-bis-(t-butyldimethylsilyl) ether | 4.0–4.8 (m, 3H), 5.4–5.8 (m, 2H). 0–0.2 (m, 12H), 0.88 (s, 18H), 0.7–1.1 (m, 3H), 1.1–3.0 (m, 19H), 3.68 (s, 3H), 4.0–4.9 (m, 3H), 5.1–6.0 (m, 4H). | 3450, 1743, 1254, 835, 774. |

EXAMPLE 8

63 mg of 7-hydroxy-5,6-dehydroprostaglandin E$_2$ methyl ester 11,15-bis-(t-butyldimethylsilyl)ether was dissolved in 5 ml of methanol, and 5 mg of 5% palladium on calcium carbonate and 10 mg of quinone were added. The mixture was stirred for 5 hours in an atmosphere of hydrogen. The reaction mixture was filtered and concentrated, and the residue was chromatographed on a silica gel (5 g) column using hexane-ethyl acetate (15:1) as an eluent to give 57 mg (yield 90%) of 7-hydroxyprostaglandin E$_2$ methyl ester 11,15-bis-(t-butyldimethylsilyl) ether having the following spectral data.

IR (neat, cm$^{-1}$): 3485, 1747, 1253, 832, 773.

NMR (CDCl$_3$, δppm): 0–0.2 (m, 12H), 0.91 (s, 18H), 0.7–1.1 (m, 3H), 1.1–2.9 (m, 19H), 3.68 (s, 3H), 4.0–4.8 (m, 3H), 5.3–5.8 (m, 4H).

EXAMPLES 9 to 12

Example 8 was followed to give the compounds shown in Table 2. The spectral data of these compounds are also shown in Table 2.

TABLE 2

| Example | Compound obtained | NMR (CDCl$_3$, δppm) | IR (cm$^{-1}$) |
|---|---|---|---|
| 9 | 7-Hydroxy-16,17,18,19,20-pentanor-15-cyclohexyl PGE$_2$ methyl ester 11,15-bis-(t-butyldimethylsilyl) ether | 0–0.2 (m, 12H), 0.88 (s, 18H), 1.1–2.9 (m, 22H), 3.69 (s, 3H), 4.0–4.8 (m, 3H), 5.3–6.0 (m, 4H). | 3450, 1744, 1251, 832, 771. |
| 10 | 7-Hydroxy-16,17,18,19,20-pentanor-15-cyclopentyl PGE$_2$ methyl ester 11,15-bis-(t-butyldimethylsilyl) ether | 0–0.2 (m, 12H), 0.89 (s, 18H), 1.1–2.9 (m, 20H), 3.68 (s, 3H), 4.0–4.8 (m, 3H), 5.3–6.0 (m, 4H). | 3470, 1745, 1251, 833, 772. |
| 11 | (17S)-7-Hydroxy-17,20-dimethyl PGE$_2$ methyl ester 11,15-bis-(t-butyldimethylsilyl) ether | 0–0.2 (m, 12H), 0.89 (s, 18H), 0.7–1.1 (m, 6H), 1.1–3.0 (m, 20H), 3.68 (s, 3H), 4.0–4.9 (m, 3H), 5.3–6.0 (m, 4H). | 3500, 1743, 1250, 830, 770. |
| 12 | (17R)-7-Hydroxy-17,20-dimethyl PGE$_2$ methyl ester 11,15-bis-(t-butyldimethylsilyl) ether | 0–0.2 (m, 12H), 0.88 (s, 18H), 0.7–1.1 (m, 6H), 1.1–3.0 (m, 20H), 3.69 (s, 3H), 4.0–4.9 (m, 3H), 5.3–6.0 (m. 4H). | 3480, 1744, 1252, 833, 773. |

EXAMPLE 13

Synthesis of (7Z) and (7E)- Δ$^7$-PGE$_1$ 11,15-bis-(t-butyldimethylsilyl)ethers 450 mg (0.75 mmole) of 7-hydroxy PGE$_1$ 11,15-bis-(t-butyldimethylsilyl) ether obtained in Referential Example 2 was dissolved in 7 ml of anhydrous dichloromethane, and 367 mg (3.0 mmoles) of 4-dimethylaminopyridine was added. With stirring under ice cooling, 116 microliters (1.5 mmoles) of methanesulfonyl chloride was added. The mixture was stirred at 0° C. for 20 minutes and then at room temperature for 16 hours. A saturated aqueous solution of sodium chloride was added, and the mixture was adjusted to pH 2 with oxalic acid. The mixture was then extracted with dichloromethane, dried over anhydrous magnesium sulfate, filtered, and concentrated. The residue was chromatographed on a silica gel column to give 216 mg (yield 48%) of (7E)- Δ$^7$-PGE$_1$ 11,15-bis-(t-butyldimethylsilyl)ether and 51 mg (yield 12%) of (7Z)- Δ$^7$-PGE$_1$ 11,15-bis-(t-butyldimethylsilyl)ether.

(7E)- Δ$^7$-PGE$_1$ bis-(t-butyldimethylsilyl)ether:
Rf=0.05 (hexane:acetone=2:1).

IR (liquid film, cm$^{-1}$): 3600–2400, 1713, 1650, 1461, 1255, 1073, 833, 772, 729.

NMR (CDCl$_3$, δppm): 0–0.2 (m, 12H), 0.84 (s, 9H), 0.87 (s, 9H), 0.7–1.1 (m, 3H), 1.0–3.0 (m, 20H), 3.2–3.7 (m, 1H), 3.8–4.3 (m, 2H), 5.3–5.7 (m, 2H), 6.66 (dt, 1H, J=7.5, 2.0), 9.0–9.8 (m, 1H).

(7Z)- Δ$^7$-PGE$_1$ bis-(t-butyl-dimethylsilyl)ether:
Rf=0.53 (hexane:acetone=2:1)

IR (liquid film, cm$^{-1}$): 3600–2400, 1740, 1648, 1460, 1254, 1077, 836, 773, 757.

NMR (CDCl$_3$, δppm): 0–0.2 (m, 12H), 0.88 (s, 9H), 0.90 (s, 9H), 0.7–1.1 (m, 3H), 1.0–3.0 (m, 20H), 3.3–3.5 (m, 1H), 3.8–4.3 (m, 2H), 4.8–6.0 (m, 1H), 5.4–5.8 (m, 2H).

EXAMPLE 14

Synthesis of (7Z) and (7E)- $\Delta^7$-PGE$_1$ methyl ester 11,15-bis-(t-butyldimethylsilyl)ethers 278 mg (0.45 mmole) of a mixture of the isomers 1 to 3 obtained in Referential Example 3 was dissolved in 3 ml of dry dichloromethane, and 332 mg (2.72 mmoles) of 4-dimethylaminopyridine was added. With stirring, 105 microliters (1.36 mmoles) of methanesulfonyl chloride was added. The mixture was stirred for 13 hours. The reaction mixture was washed with a saturated aqueous solution of sodium hydrogen carbonate. The aqueous layer was extracted with ether three times. The organic layers were combined, washed with a saturated aqueous solution of sodium chloride, dried over anhydrous magnesium sulfate, filtered, and concentrated. The residue was chromatographed on a silica gel column (10 g) using hexane-ethyl acetate (30:1) as an eluent to give 222 mg (yield 82%) of (7E)- $\Delta^7$-PGE$_1$ methyl ester 11,15-bis-(t-butyldimethylsilyl)ether and 8 mg (yield 3%) of (7Z)- $\Delta^7$-PGE$_1$ methyl ester 11,15-bis-(t-butyldimethylsilyl)ether.

(7Z)- $\Delta^7$-PGE$_1$ methyl ester 11,15-bis-(t-butyldimethylsilyl)ether:

Rf=0.50 (hexane:ethyl acetate=5:1),

NMR (CDCl$_3$, $\delta$ppm): 0–0.2 (m, 12H), 0.88 (s, 9H), 0.91 (s, 9H), 0.7–1.1 (m, 3H), 1.1–3.0 (m, 20H), 3.0–3.5 (m, 1H), 3.69 (s, 3H), 3.7–4.4 (m, 2H), 5.4–6.1 (m, 3H).

(7E)- $\Delta^7$-PGE$_1$ methyl ester 11,15-bis-(t-butyldimethylsilyl)ether:

Rf=0.46 (hexane:ethyl acetate =5:1),

NMR (CDCl$_3$, $\delta$ppm): 0–0.2 (m, 12H), 0.89 (s, 9H), 0.91 (s, 9H), 0.7–1.1 (m, 3H), 1.1–2.8 (m, 20H), 3.3–3.6 (m, 1H), 3.69 (s, 3H), 3.8–4.4 (m, 2H), 5.4–5.7 (m, 2H), 6.81 (dt, 1H).

EXAMPLE 15

Synthesis of $\Delta^7$-PGE$_1$ methyl ester 11,15-bis-(t-butyldimethylsilyl)ether (1) 30 mg (49 micromoles) of 7-hydroxyprostaglandin E$_1$ methyl ester 11,15-bis-(t-butyldimethylsilyl)ether obtained as isomer 1 in Referential Example 1 was dissolved in 0.5 ml of anhydrous pyridine, and with stirring at room temperature, 11.4 microliters (147 micromoles) of methanesulfonyl chloride was added. The mixture was stirred for 2 hours. The reaction mixture was poured into ice water, and extracted with pentane. The organic layer was washed with water, dried over anhydrous sodium sulfate, filtered, and concentrated to give 31 mg of 7-methanesulfonyloxy PGE$_1$ methyl ester 11,15-bis-(t-butyldimethylsilyl)ether as an oil.

NMR (CDCl$_3$, $\delta$ppm): 3.08 (s, 3H), 3.65 (s, 3H), 3.8–4.4 (m, 2H), 5.3–5.8 (m, 3H).

IR (liquid film, cm$^{-1}$): 1729, 1363, 1253, 1175, 833.

(2) 31 mg of 7-methanesulfonyloxy PGE$_1$ methyl ester 11,15-bis-(t-butyldimethylsilyl)ether obtained in (1) above was dissolved in 1 ml of dichloromethane, and 30 mg of 4-N,N-dimethylaminopyridine was added. The mixture was stirred at 30° C. for 5 hours. A saturated aqueous solution of sodium chloride was added, and the mixture was extracted with ethyl acetate. The extract was dried over anhydrous sodium sulfate, filtered, and concentrated. The residue was chromatographed on a silica gel column (2 g) using hexane-ethyl acetate (20:1) as an eluent to give 18 mg (yield 62%) of $\Delta^7$-PGE$_1$ methyl ester 11,15-bis-(t-butyldimethylsilyl)ether.

EXAMPLE 16

Synthesis of $\Delta^7$-PGE$_1$ methyl ester 11,15-bis-(tetrahydropyranyl)ether

A 10 ml of an eggplant-shaped flask was charged with 167 mg (0.302 mmole) of 7-hydroxy-PGE$_1$ methyl ester 11,15-bis-(tetrahydropyranyl)ether, and 225 ml of dry dichloromethane and 220 mg (1.80 mmoles) of 4-dimethylaminopyridine were added. The mixture was cooled over an ice bath, and 70 microliters (0.90 mmole) of methanesulfonyl chloride was added dropwise. The ice bath was removed, and the mixture was stirred at room temperature (24° C.) for 11 hours. The reaction mixture was added to 15 ml of a saturated aqueous solution of sodium hydrogen carbonate, and the mixture was shaken and extracted with three 10 ml portions of dichloromethane. The organic layers were combined, washed with 10% hydrochloric acid and a saturated aqueous solution of sodium chloride, dried over anhydrous magnesium sulfate and concentrated. The residue was chromatographed over a silica gel column (7 g) using hexane-ethyl acetate (4:1) as an eluent to give 67.4 mg (yield 42%) of $\Delta^7$-PGE$_1$ methyl ester 11,15-bis-(tetrahydropyranyl)ether [mixture of (17E) and 17Z)].

NMR (CDCl$_3$, $\delta$ppm): 6.72 (dt, J=7.8, 2.0 Hz, 1H), 5.8–5.1 (m, 2H), 4.8–4.5 (m, 2H), 4.3–3.2 (m, 10H), 2.6–2.0 (m, 6H), 0.88 (t, 3H).

IR (neat, cm$^{-1}$): 1743, 1734, 1653.

Mass (75 eV, m/e): 534 (M+).

EXAMPLE 17

Synthesis of $\Delta^7$-PGE$_1$ methyl ester 16 mg (30 micromoles) of $\Delta^7$-PGE$_1$ methyl ester 11,15-bis-(tetrahydropyranyl)ether obtained in Example 16 was dissolved in a mixture of 0.3 ml acetic acid, 0.1 ml water and 0.1 ml tetrahydrofuran, and reacted at room temperature for 24 hours. After the reaction, toluene was added, and the solvent was evaporated under reduced pressure to form 10 mg of a crude product. The crude product was purified by thin-layer chromatography (ethyl acetate: cyclohexane=4:6) to give 4.8 mg (13 micromoles; yield 43%) of the desired $\Delta^7$-PGE$_1$ methyl ester [mixture of (7E) and (7Z)].

NMR (CDCl$_3$, $\delta$ppm): 6.72 (1H, dt, J=7.8, 2.0 Hz), 5.8–5.1 (2H, m), 4.3–3.6 (2H, m), 3.65 (3H, s), 3.2–1.0 (23H), 0.9 (3H, t, J=7.0).

IR (neat, cm$^{-1}$): 3450, 1743, 1730, 1650.

Mass (20 eV, m/e): 348 (M+—H$_2$O).

EXAMPLE 18

Synthesis of $\Delta^7$-5,6-dehydro-PGE$_2$ methyl ester 11,15-bis-(t-butyldimethylsilyl)ether 209 mg (0.343 mmole) of 7-hydroxy-5,6-dehydro-PGE$_2$ methyl ester 11,15-bis-(t-butyldimethylsilyl)ether [mixture of (7S) and (7R)] and 127 mg (1.04 mmoles) of 4-dimethylaminopyridine were dissolved in 4 ml of dry dichloromethane, and 40 microliters (0.52 mmole) of methanesulfonyl chloride was added dropwise at room temperature (about 25° C.). After stirring the mixture for 30 minutes, 10 microliters (0.13 mmole) of methanesulfonyl chloride was added, and the mixture was stirred for 15 minutes. The reaction mixture was added to 20 ml of a saturated aqueous solution of ammonium chloride and shaken to separate the organic layer. The aqueous layer was extracted with two 10 ml portions of dichloromethane. The organic layers were combined, washed with 10% hydrochloric acid, dried over anhydrous magnesium sulfate, and concentrated. The residue was chromatographed on a column of silica gel (10 g) using hexane-ether (5:1) as an eluent to give 124 mg (61%) of $\Delta^7$-5,6-dehydro-PGE$_2$ methyl ester 11,15-bis-(t-butyldimethylsilyl)ether [mixture of (7E) and (7S)].

NMR (CDCl$_3$, δppm): 6.52 (br, 1H), 5.5–5.4 (m, 2H), 4.19 (m, 1H), 4.00 (br, 1H), 3.59 (s, 3H), 3.55 (br, 1H), 2.5–2.3 (m, 6H), 2.0–1.1 (m), 0.9–0.8 (m), 0.0–0.1 (m).

IR (neat, cm$^{-1}$): 2216, 1750, 1731, 1621.

EXAMPLE 19

Synthesis of $\Delta^7$-5,6-dehydro-PGE$_2$ methyl ester 11,15-bis-(t-butyldimethylsilyl)ether (1) 200 mg (328 micromoles) of (7R)-7-hydroxy-5,6-dehydro-PGE$_2$ methyl ester 11,15-bis-(t-butyldimethylsilyl)ether was dissolved in 2 ml of anhydrous pyridine, and with stirring under ice cooling, 76 microliters (985 micromoles) of methanesulfonyl chloride was added. The mixture was stirred at 0° C. for 1.5 hours. The reaction mixture was poured into ice water, and extracted with pentane. The organic layer was washed with a saturated aqueous solution of sodium chloride, dried over anhydrous sodium sulfate, filtered, and concentrated to give 210 mg of an oil containing (7R)-7-methanesulfonyloxy-5,6-dehydro-PGE$_2$ methyl ester 11,15-bis-(t-butyldimethylsilyl)ester.

NMR (CDCl, δppm): 3.04 (s, 3H), 3.65 (s, 3H), 3.8–4.4 (m, 2H), 5.3–5.8 (m, 3H).

IR (liquid film, cm$^{-1}$): 1744, 1365, 1252, 1175, 834.

(2) 210 mg of (7R)-7-methanesulfonyloxy-5,6-dehydro-PGE$_2$ methyl ester 11,15-bis-(t-butyldimethylsilyl)ether obtained in (1) above was dissolved in 3 ml of dichloromethane, and 200 mg of 4-N,N-dimethylaminopyridine was added. The mixture was stirred at 30° C. for 3 hours. A saturated aqueous solution of sodium chloride was added, and the mixture was extracted with ethyl acetate. The extract was dried over anhydrous sodium sulfate, filtered, and concentrated. The residue was chromatographed on a silica gel column (10 g) using hexane-ethyl acetate (15:1) as an eluent to give 134 mg (yield 69%) of $\Delta^7$-5,6-dehydro-PGE$_2$ methyl ester 11,15-bis-(t-butyldimethylsilyl)ether.

EXAMPLE 20

Synthesis of $\Delta^7$-5,6-dehydro-PGE$_2$ methyl ester 45 mg of $\Delta^7$-5,6-dehydro-PGE$_2$ methyl ester 11,15-bis-(t-butyldimethylsilyl)ether [mixture of (7E) and (7Z)] was dissolved in a mixture of 0.8 ml acetic acid, 0.4 ml water and 0.4 ml tetrahydrofuran, and the solution was stirred at room temperature for 48 hours. Toluene was added to the reaction mixture, and the solvent was evaporated under reduced pressure. As a crude product, 25 mg of an oil was obtained. The oil was purified by thin-layer chromatography (cyclohexane/ethyl acetate=1/1) to give 8 mg (yield 52%) of the desired $\Delta^7$-5,6-dehydro-PGE$_2$ methyl ester [mixture of (7E) and (7Z)].

NMR (CDCl$_3$, δppm): 6.55 (1H, m), 5.55 (2H, m), 3.7–4.4 (2H, m), 3.65 (3H, s), 1.0–2.7 (19H), 0.9 (2H, t, J=7Hz).

IR (CHCl$_3$, cm$^{-1}$): 3450, 2230, 1720, 1615.

Mass (20 eV, m/e): 344 (M$^+$—H$_2$O).

EXAMPLE 21

Synthesis of (7E)- $\Delta^7$-PGE$_1$ 22 mg (38 micromoles) of (7E)- $\Delta^7$-PGE$_1$ 11,15-bis-(t-butyldimethylsilyl) ether and 1.0 ml of a hydrogen fluorideacetonitrile solution (prepared by adding 10 ml of acetonitrile to 0.5 ml of 47% hydrofluoric acid) were stirred at room temperature for 20 minutes. A saturated aqueous solution of sodium hydrogen carbonate was added to the reaction mixture. The mixture was acidified with oxalic acid, and then extracted with ethyl acetate. The organic layer was washed with a saturated aqueous solution of sodium chloride, dried over anhydrous magnesium sulfate, filtered, and concentrated. The residue was purified by silica gel thin-layer chromatography (using hexane/acetone/acetic acid=1/1/0.01 as a developing solvent) to give 3.7 mg (yield 37%) of (7E)- $\Delta^7$-PGE$_1$.

Rf=0.47 (hexane:acetone=1:2).

IR (CHCl$_3$, cm$^{-1}$): 3400, 1715, 1642, 973.

NMR (CDCl$_3$, δppm): 0.88 (br. t, 3H), 1.0–1.9 (m, 14H), 1.9–2.9 (m, 5H), 2.9–3.9 (m, 5H), 3.9–4.5 (m, 2H), 5.3–5.9 (m, 2H), 6.7–7.0 (m, 1H).

EXAMPLES 22 to 38

Example 13 was followed to give the compounds shown in Table 3. The spectral data of these compounds are also shown in Table 3.

TABLE 3

| Example | Compound formed | NMR (CDCl$_3$, δppm) | IR (cm$^{-1}$) |
|---|---|---|---|
| 22 | $\Delta^7$-15-methyl PGE$_1$ methyl ester 11,15-bis-(t-butyldimethylsilyl) ether | 0–0.2 (m, 12H), 0.88 (s, 18H), 0.7–1.1 (m, 3H), 1.1–3.0 (m, 23H), 3.3–3.7 (m, 1H), 3.68 (s, 3H), 3.7–4.4 (m, 2H), 5.4–5.8 (m, 2H), 6.8 (dt, 1H). | 1742, 1728, 1655, 1255, 834, 774. |
| 23 | $\Delta^7$-16,17,18,19,20-pentanor-15-cyclohexyl PGE$_1$ methyl ester 11,15-bis-(t-butyldimethylsilyl) ether | 0–0.2 (m, 12H), 0.89 (s, 18H), 1.1–3.0 (m, 23H), 3.69 (s, 3H), 3.3–3.7 (m, 1H), 3.7–4.4 (m, 2H), 5.3–5.8 (m, 2H), 6.85 (dt, 1H). | 1743, 1729, 1655, 1254, 832, 772. |
| 24 | $\Delta^7$-16,17,18,19,20-pentanor-15-cyclopentyl PGE$_1$ methyl ester 11,15-bis-(t-butyldimethylsilyl) ether | 0–0.2 (m, 12H), 0.88 (s, 18H), 1.1–3.0 (m, 21H), 3.68 (s, 3H), 3.3–3.7 (m, 1H), 3.7–4.4 (m, 2H), | 1741, 1728, 1654, 1253, 833, 772. |

TABLE 3-continued

| Example | Compound formed | NMR (CDCl$_3$, δppm) | IR (cm$^{-1}$) |
|---|---|---|---|
| | | 5.3–5.8 (m, 2H), 6.83 (dt, 1H). | |
| 25 | Δ$^7$-17,18,19,20-tetranor-16-cyclohexyl PGE$_1$ methyl ester 11,15-bis-(t-butyldimethylsilyl) ether | 0–0.2 (m, 12H), 0.89 (s, 18H), 1.1–2.9 (m, 25H), 3.68 (s, 3H), 3.25–3.65 (m, 1H), 3.7–4.4 (m, 2H), 5.3–5.8 (m, 2H), 6.82 (dt, 1H). | 1743, 1730, 1656, 1255, 835, 775. |
| 26 | (17S)-Δ$^7$-17,20-dimethyl PGE$_1$ methyl ester 11,15-bis-(t-butyldimethylsilyl) ether | 0–0.2 (m, 12H), 0.88 (s, 18H), 0.7–1.1 (m, 6H), 1.1–2.9 (m, 21H), 3.67 (s, 3H), 3.25–3.7 (m, 1H), 3.7–4.4 (m, 2H), 5.3–5.8 (m, 2H), 6.83 (dt, 1H). | 1742, 1729, 1652, 1254, 832, 771. |
| 27 | (17R)-Δ$^7$-17,20-dimethyl PGE$_1$ methyl ester 11,15-bis-(t-butyldimethylsilyl) ether | 0–0.2 (m, 12H), 0.88 (s, 18H), 0.7–1.1 (m, 6H), 1.1–2.9 (m, 21H), 3.68 (s, 3H), 3.3–3.7 (m, 1H), 3.75–4.4 (m, 2H), 5.3–5.8 (m, 2H), 6.83 (dt, 1H). | 1744, 1730 1655, 1256, 835, 774. |
| 28 | Δ$^7$-17,17,20-trimethyl PGE$_1$ methyl ester 11,15-bis-(t-butyldimethylsilyl) ether | 0–0.2 (m, 12H), 0.88 (s, 18H), 0.91 (s, 6H), 0.7–1.1 (m, 3H), 1.1–3.0 (m, 20H), 3.67 (s, 3H), 3.25–3.6 (m, 1H), 3.7–4.4 (m, 2H), 5.3–5.8 (m, 2H), 6.79 (dt, 1H). | 1743, 1729, 1655, 1254, 834, 773. |
| 29 | Δ$^7$-16,16-dimethyl PGE$_1$ methyl ester 11,15-bis-(t-butyldimethylsilyl) ether | 0–0.2 (m, 12H), 0.88 (s, 18H), 0.92 (s, 6H), 0.7–1.1 (m, 3H), 1.1–3.0 (m, 18H), 3.3–3.7 (m, 1H), 3.68 (s, 3H), 3.75–4.45 (m, 2H), 5.4–5.8 (m, 2H), 6.8 (dt, 1H). | 1742, 1728, 1654, 1254, 834, 773. |
| 30 | Δ$^7$-18-oxa PGE$_1$ methyl ester 11,15-bis-(t-butyldimethylsilyl) ether | 0–0.2 (m, 12H), 0.87 (s, 18H), 1.15 (t, 3H), 1.1–3.0 (m, 14H), 3.69 (s, 3H), 3.2–4.4 (m, 7H), 5.8 (m, 2H), 6.79 (dt, 1H). | 1743, 1730 1653, 1255, 833, 774. |
| 31 | Δ$^7$5,6-dehydro-16,17,18,19,20-pentanor-15-cyclohexyl-PGE$_2$ methyl ester 11,15-bis-(t-butyldimethylsilyl) ether | 0–0.2 (m, 12H), 0.88 (s, 18H), 1.1–2.5 (m, 19H), 3.3–3.7 (m, 1H), 3.68 (s, 3H), 3.75–4.5 (m, 2H), 5.4–5.8 (m, 2H), 6.4–6.6 (m, 1H). | 2216, 1750 1731, 1621, 1254, 834, 773. |
| 32 | Δ$^7$-5,6-dehydro-16,17,18,19,20-pentanor-15-cyclopentyl-PGE$_2$ methyl ester 11,15-bis-(t-butyldimethylsilyl) ether | 0–0.2 (m, 12H), 0.89 (s, 18H), 1.1–2.5 (m, 17H), 3.3–3.65 (m, 1H), 3.67 (s, 3H), 3.75–4.5 (m, 2H), 5.4–5.9 (m, 2H), 6.4–6.7 (m, 1H). | 2218, 1749 1730, 1620, 1254, 833, 771. |
| 33 | (17S)-5,6-dehydro-Δ$^7$-17,20-dimethyl PGE$_2$ methyl ester 11,15-bis-(t-butyldimethylsilyl) ether | 0–0.2 (m, 12H), 0.89 (s, 18H), 0.7–1.1 (m, 6H), 1.1–2.5 (m, 17H), 3.3–3.7 (m, 1H), 3.68 (s, 3H), 3.7–4.5 (m, 2H), 5.3–5.8 (m, 2H), 6.4–6.7 (m, 1H). | 2220, 1749, 1731, 1621, 1255, 833, 772. |

TABLE 3-continued

| Example | Compound formed | NMR (CDCl$_3$, δppm) | IR (cm$^{-1}$) |
|---|---|---|---|
| 34 | (17R)-Δ$^7$-5,6-dehydro-17,20-dimethyl PGE$_2$ methyl ester 11,15-bis-(t-butyldimethylsilyl) ether | 0–0.2 (m, 12H), 0.88 (s, 18H), 0.7–1.1 (m, 6H), 1.1–2.5 (m, 17H), 3.3–3.7 (m, 1H), 3.67 (s, 3H), 3.7–4.4 (m, 2H), 5.3–5.8 (m, 2H), 6.4–6.7 (m, 1H). | 2220, 1750, 1731, 1620, 1253, 831, 771. |
| 35 | Δ$^7$-16,17,18,19,20-pentanor-15-cyclohexyl PGE$_2$ methyl ester 11,15-bis-(t-butyldimethylsilyl) ether | 0–0.2 (m, 12H), 0.89 (s, 18H), 1.1–2.5 (m, 19H), 3.3–3.7 (m, 1H), 3.67 (s, 3H), 3.7–4.5 (m, 2H), 5.3–6.3 (m, 3H), 6.3–6.7 (m, 1H). | 1748, 1730, 1625, 1250, 833, 772. |
| 36 | Δ$^7$-16,17,18,19,20-pentanor-15-cyclopentyl-PGE$_2$ methyl ester 11,15-bis-(t-butyldimethylsilyl) ether | 0–0.2 (m, 12H), 0.88 (s, 18H), 1.1–2.5 (m, 17H), 3.3–3.7 (m, 1H), 3.67 (s, 3H), 3.7–4.5 (m, 2H), 5.3–5.8 (m, 2H), 6.4–6.7 (m, 1H). | 1747, 1729, 1626, 1252, 834, 773. |
| 37 | (17S)- Δ$^7$-17,20-dimethyl PGE$_2$ methyl ester 11,15-bis-(t-butyldimethylsilyl) ether | 0–0.2 (m, 12H), 0.88 (s, 18H), 0.7–1.1 (m, 6H), 1.1–2.5 (m, 17H), 3.3–3.7 (m, 1H), 3.68 (s, 3H), 3.7–4.5 (m, 2H), 5.3–6.3 (m, 3H), 6.3–6.7 (m, 1H). | 1748, 1730, 1625, 1251, 834, 773. |
| 38 | (17R)- Δ$^7$-17,20-dimethyl PGE$_2$ methyl ester 11,15-bis-(t-butyldimethylsilyl) ether | 0–0.2 (m, 12H), 0.88 (s, 18H), 0.7–1.1 (m, 6H), 1.1–2.5 (m, 17H), 3.3–3.7 (m, 1H), 3.67 (s, 3H), 3.7–4.5 (m, 2H), 5.3–6.3 (m, 3H), 6.3–6.7 (m, 1H). | 1749, 1731, 1625, 1250, 832, 771. |

EXAMPLE 39

Synthesis of PGE$_1$ methyl ester 11,15-bis-(t-butyldimethylsilyl) ether 160 mg (269 micromoles) of (7E)- Δ$^7$-PGE$_1$ methyl ester 11,15-bis-(t-butyldimethylsilyl) ether obtained in Example 14 was dissolved in 1 ml of isopropanol, and 0.2 ml of acetic acid was added. With stirring, 800 mg of zinc powder was added. The mixture was stirred at 50° C. for 2 hours. A saturated aqueous solution of sodium hydrogen carbonate was added to the reaction mixture, and the mixture was extracted with ethyl acetate. The aqueous layer was extracted twice with ethyl acetate. The organic layers were combined, washed with a saturated aqueous solution of sodium chloride, dried over anhydrous magnesium sulfate, filtered, and concentrated. The residue was chromatographed on a column of silica gel (10 g) using hexane-ethyl acetate (30:1) as an eluent to give 97 mg (yield 60%) of the desired PGE$_1$ methyl ester 11,15-bis-(t-butyldimethylsilyl) ether.

NMR (CDCl$_3$, δppm): 0–0.2 (m, 12H), 0.89 (s, 18H), 0.7–1.1 (m, 3H), 1.1–3.0 (m, 24H), 3.70 (s, 3H), 3.7–4.4 (m, 2H), 5.4–5.7 (m, 2H).

IR (neat, cm$^{-1}$): 1743, 1253, 835, 774.

EXAMPLE 40

Synthesis of PGE$_1$ 11,15-bis-(t-butyldimethylsilyl) ether 47 mg (81 micromoles) of (7E)- Δ$^7$-PGE$_1$ 11,15-bis-(t-butyldimethylsilyl) ether was dissolved in 2 ml of acetic acid. 400 mg (6.1 mmoles) of zinc powder was added at room temperature, and the mixture was stirred for 22 hours at room temperature. The reaction mixture was poured into ice water and extracted with ethyl acetate. The organic layer was washed with a saturated aqueous solution of sodium chloride, dried over anhydrous magnesium sulfate, filtered, and concentrated. The residue was chromatographed on a silica gel column to give 21 mg (yield 45%) of PGE$_1$ 11,15-bis-(t-butyldimethylsilyl) ether.

Rf=0.58 (hexane:ethyl acetate=1:1)

IR (liquid film, cm$^{-1}$): 3600–2400, 1743, 1710, 1460, 1253, 1098, 834, 774.

NMR (CDCl$_3$, δppm): 0–0.2 (m, 12H), 0.88 (s, 9H), 0.90 (s, 9H), 0.7–1.1 (m, 3H), 1.0–2.9 (m, 24H), 3.9–4.4 (m, 2H), 4.8–5.8 (m, 1H), 5.4–5.7 (m, 2H).

EXAMPLE 41

Synthesis of PGE$_1$ 11,15-bis-(t-butyldimethylsilyl) ether

From 30 mg of (7Z)- Δ$^7$-PGE$_1$ 11,15-bis-(t-butyldimethylsilyl) ether, 10 mg (yield 33%) of PGE$_1$ 11,15-bis-(t-butyldimethylsilyl) ether was obtained by the same operation as in Example 10.

EXAMPLE 42

Synthesis of PGE$_1$ methyl ester 11,15-bis-(t-butyldimethylsilyl) ether 17.4 mg (29.4 micromoles) of $\Delta^7$-5,6-dehydro-PGE$_2$ methyl ester 11,15-bis-(t-butyldimethylsilyl) ether obtained in Example 18 was dissolved in 1 ml of methanol, and Raney nickel W-2 was added in an amount corresponding to one-third of an earpick. Under a hydrogen atmosphere, the mixture was stirred at room temperature (29° C.) for 1 hour. The catalyst was removed by using Celite, and the filtrate was concentrated and chromatographed on a column of silica gel (10 g) using hexane-ether (6:1) as an eluent to give 6.7 mg (38%) of PGE$_1$ methyl ester 11,15-bis-(t-butyldimethylsilyl) ether.

NMR (CDCl$_3$, δppm): 5.6–5.4 (m, 2H), 4.2–3.8 (m, 2H), 3.66 (s, 3H), 2.64 (dd, 1H, J=7.2, 18.4 Hz), 2.4–1.8 (m, 4H), 1.7–1.0 (m), 1.0–0.8 (m, 21H), 0.1–0.0 (m).

IR (neat, cm$^{-1}$): 1750.

EXAMPLE 43

Synthesis of PGE$_1$ 10 mg (17 micromoles) of PGE$_1$ 11,15-bis-(t-butyldimethylsilyl) ether obtained in Example 40 was dissolved in 1.0 ml of a hydrogen fluoride-acetonitrile solution (prepared by adding 0.5 ml of 47% hydrofluoric acid to 10 ml of acetonitrile), and the solution was stirred at room temperature for 20 minutes. After adding a 10% aqueous solution of sodium hydrogen carbonate, the mixture was adjusted to pH 3 with oxalic acid. It was then extracted with ethyl acetate. The organic layers were combined, washed with a saturated aqueous solution of sodium chloride, dried over anhydrous magnesium sulfate, filtered, and concentrated. The residue was purified by silica gel thin-layer chromatography to give 3.9 mg (yield 69%) of PGE$_1$.

Melting point: 114.8°–115.7° C.

Specific rotation $[\alpha]_D^{25}$: −53.3° (c=0.63, THF)

EXAMPLE 44

Synthesis of PGE$_1$ methyl ester 3 ml of a hydrogen fluoride-acetonitrile solution (prepared by adding 0.5 ml of 47% hydrofluoric acid to 10 ml of acetonitrile) was added to 100 mg (168 micromoles) of PGE$_1$ methyl ester 11,15-bis-(t-butyldimethylsilyl) ether obtained in Example 39, and the mixture was stirred for 40 minutes. A saturated aqueous solution of sodium hydrogen carbonate was added, and the mixture was extracted with ether. The organic layers were combined, washed with a saturated aqueous solution of sodium chloride, dried over anhydrous magnesium sulfate, filtered, and concentrated. The residue was purified by silica gel thin-layer chromatography using ethyl acetate as a developing solvent give 15 mg (yield 24%) of PGE$_1$ methyl ester.

Rf=0.29 (ethyl acetate).

NMR (CDCl$_3$, δppm): 0.88 (br. t, 3H), 0.9–3.2 (m, 26H), 3.67 (s, 3H), 3.7–4.4 (m, 2H), 5.3–5.8 (m, 2H).

EXAMPLE 45

Synthesis of PGE$_1$ 50 ml of a mixed solution of 0.1M NaCl and 0.05M CaCl$_2$ was added to 5 g of lipase (from porcine pancreas), and the mixture was stirred at 0° C. for 3.5 hours. The mixture was then centrifuged at 0° C. and 9000 rpm for 30 minutes. The supernatant liquid was adjusted to pH 7.0 with 1N NaOH and 0.1N NaOH, and then transferred to a sonicating reactor. 15 mg (41 micromoles) of PGE$_1$ methyl ester and 3 ml of acetone were added, and the reaction was carried out for 30 minutes. The reaction mixture was poured into 300 ml of acetone, and concentrated. Ammonia sulfate was added, and the mixture was extracted with ethyl acetate. The extract was dried over anhydrous magnesium sulfate, filtered, and concentrated. The residue was purified by silica gel thin-layer chromatography (0.25 mm, 20 cm×20 cm, developing solvent ethyl acetate/acetic acid=100/0.5; developed three times) to give 12.9 mg (yield 89%) of PGE$_1$. Recrystallization from ethyl acetate-hexane afforded 9.5 mg (yield 66%) of white needles.

Rf=0.73 (THF).

Melting point: 114.8°–115.7° C.

$[\alpha]_D^{25}$: −53.3° (c=0.63, THF).

EXAMPLE 46

Synthesis of PGE$_1$ 37 mg of PGE$_1$ methyl ester obtained in Example 44 was dissolved in 0.45 ml of acetone, and 4.5 ml of a 0.1M phosphate buffer (pH 8) was added. Thereafter 45 microliters of a suspension of esterase (from porcine liver) in a 3.2M ammonium sulfate solution was added, and the mixture was stirred at room temperature for 5 hours. With ice cooling, the mixture was adjusted to pH 4 with dilute hydrochloric acid. Ammonium sulfate was added, and the mixture was extracted with ethyl acetate. The organic layer was dried over anhydrous sodium sulfate, filtered, and concentrated. The resulting crude crystals were recrystallized from ethyl acetate to give 30 mg (yield 85%) of PGE$_1$.

EXAMPLES 47 to 50

Using the compounds obtained in Examples 23, 24, 26 and 29, respectively, Example 39 was followed. The compounds indicated in Table 4 were obtained. The spectral data of these compounds are also shown in Table 4.

TABLE 4

| Example | Compound obtained | NMR (CDCl$_3$, δppm) | IR (cm$^{-1}$) |
|---|---|---|---|
| 47 | 16,17,18,19,20-pentanor-15-cyclohexyl PGE$_1$ methyl ester 11,15-bis-(t-butyl-dimethylsilyl) ether | 0–0.2 (m, 12H), 0.89 (s, 18H), 1.0–3.0 (m, 27H), 3.68 (s, 3H), 3.7–4.4 (m, 2H), 5.4–5.8 (m, 2H). | 1741, 1254 834, 772. |
| 48 | 16,17,18,19,20-pentanor-15-cyclopentyl PGE$_1$ methyl ester 11,15-bis-(t-butyl-dimethylsilyl) ether | 0–0.2 (m, 12H), 0.89 (s, 18H), 1.0–2.9 (m, 25H), 3.67 (s, 3H), 3.7–4.4 (m, 2H), 5.4–5.8 (m, 2H). | 1742, 1253 833, 772. |

TABLE 4-continued

| Example | Compound obtained | NMR (CDCl$_3$, δppm) | IR (cm$^{-1}$) |
|---|---|---|---|
| 49 | (17S)-17,20-dimethyl PGE$_1$ methyl ester 11,15-bis-(t-butyldimethylsilyl) ether | 0–0.2 (m, 12H), 0.89 (s, 18H), 0.7–1.1 (m, 6H), 1.1–3.0 (m, 25H), 3.68 (s, 3H), 3.7–4.4 (m, 2H), 5.4–5.8 (m, 2H). | 1741, 1253 834, 773. |
| 50 | 17,17,20-trimethyl PGE$_1$ methyl ester 11,15-bis-(t-butyldimethylsilyl) ether | 0–0.2 (m, 12H), 0.89 (s, 18H), 0.91 (s, 6H), 0.7–1.1 (m, 3H), 1.1–3.0 (m, 24H), 3.67 (s, 3H), 3.7–4.4 (m, 2H), 5.4–5.8 (m, 2H). | 1743, 1255 834, 773. |

EXAMPLES 51 to 53

The compounds obtained in Examples 31, 32 and 33, respectively, were subjected to reduction in the same way as in Example 42 to give 16,17,18,19,20-pentanor-15-cyclohexyl PGE$_1$ methyl ester 11,15-bis-(t-butyldimethylsilyl) ether (Example 51), 16,17,18,19,20-pentanor-15-cyclopentyl PGE$_1$ methyl ester 11,15-bis-(t-butyldimethylsilyl) ether (Example 52), and 17(S)-17,20-dimethyl PGE$_1$ methyl ester 11,15-bis-(t-butyldimethylsilyl) ether (Example 53). The spectral data of these compounds agreed with those given in Table 4.

EXAMPLE 54

Measurement of antiulcer activity

A test on an ethanol-induced ulcer was carried out in the following manner.

SD-strain rats (6 weeks old; body weight 145–160 g) were caused to fast for 24 hours, and then a solution of each of the test compounds shown in Table 5 in a physiological saline buffered with phosphate (pH 7.5) was orally administered to the rats. Thirty minutes later, 75% ethanol was orally administered to the rats in a dose of 2 ml/kg. One hour later, the rats were knocked out to death. The stomach was extracted from each rat, and 10 ml of saline was injected into the stomach. The stomach was then fixed in 1% formalin for about 20 minutes, and then incised along the greater curvature, and the length of an ulcer generated at the body of the stomach was measured by using a stereoscope and made an ulcer index.

The control group was given a physiological saline buffered with phosphate (pH 7.5) and 75% ethanol.

The results are shown in Table 5.

TABLE 5

| Test compound | Dose (oral) | Number of subjects | Ulcer index (mm) | Percent inhibition (%) |
|---|---|---|---|---|
| Control | — | 8 | 48.4 ± 8.9 | — |
| 7-Hydroxy-5,6-dehydro-PGE$_2$-methyl ester | 1.0 mg/kg | 5 | 36.0 ± 15.4 | 24.4 |
| Δ$^7$-5,6-dehydro-PGE$_2$ methyl ester | 1.0 mg/kg | 5 | 21.0 ± 9.0 | 56.6 |

EXAMPLE 55

Measurement of the activity of inhibiting gastric juice secretion

SD-strain rats (7 weeks old; body weight 200–220 g) were caused to fast for 24 hours, anesthetized with urethane (1.2 g/kg i.p.), and fixed at the back. The neck portion was incised. A tracheal cannula was inserted and the esophagus was ligated. The abdomen was incised mesially to expose the stomach, and the pyloric portion was ligated. A perfusion cannula was inserted into the stomach from the proventriculus. After the operation, the inside of the stomach was fully washed with physiological saline, and then perfused with physiological saline at a rate of 10 ml/min. The amount of gastric juice secreted was measured by means of 0.01N NaOH at a pH of 4.0 using a pH stat, and recorded on a recorder. To determine the activity of the test compound to inhibit gastric acid secretion, pentagastrin (1 μg/kg-hr) was continuously injected intravenously, and after the acid secretion became constant, the test compound was subcutaneously injected. The test compound was used as a 10 mg/ml ethanol solution diluted with a phosphate buffer (pH 7.4).

The results are shown in Table 6.

TABLE 6

| Test compound | Dose (subcutaneos) | Number of subjects | Acid secretion inhibition (%) |
|---|---|---|---|
| Δ$^7$-5,6-dehydro-PGE$_2$ methyl ester | 1 mg/kg | 3 | 25.4 |

What we claim is:

1. A Δ$^7$-prostaglandin E represented by the following formula

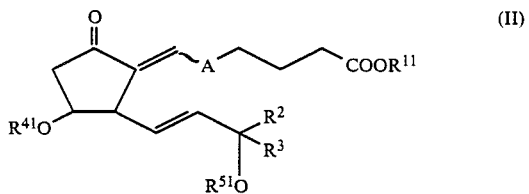

(II)

wherein R$^{11}$ represents a hydrogen atom, an alkyl group having 1 to 10 carbon atoms or a tri(C$_{1-7}$ hydrocarbon) silyl group, R$^2$ represents an alkyl group having 1 to 10 carbon atoms or a 5- or 6-membered cycloalkyl group wherein the alkyl group or cycloalkyl group for R$^2$ is unsubstituted or substituted with a lower alkyl group, a lower alkoxy group, a cycloalkyl group, ethenyl, phenyl, phenoxy, trifluorophenyl or trifluoromethyl, R$^3$ represents a hydrogen atom or a methyl group, R$^{41}$ and R$^{51}$ are identical or different and each represents a hydrogen atom or a protective group for the hydroxyl group, and A represents the group —CH$_2$CH$_2$—, —CH=CH— or —C≡C—, wherein the protective group for the hydroxyl group is a tri(C$_{1-7}$ hydrocarbon)silyl group or a group capable of forming an acetal linkage with the oxygen atom of the hydroxyl group.

2. The $\Delta^7$-prostaglandin E of claim 1 which is represented by the following formula

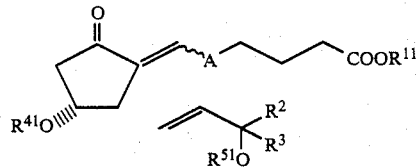

wherein R$^{11}$, R$^2$, R$^3$, R$^{41}$, R$^{51}$ and A are as defined.

3. The $\Delta^7$-prostaglandin E of claim 1 which is represented by the following formula

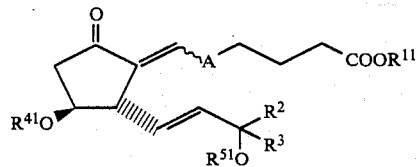

wherein R$^{11}$, R$^2$, R$^3$, R$^{41}$, R$^{51}$ and A are as defined.

4. The $\Delta^7$-prostaglandin E of any one of claims 1 to 3 wherein when R$^2$ is said alkyl group or substituted alkyl group, the alkyl group has 5 to 8 carbon atoms.

5. The $\Delta^7$-prostaglandin E of any one of claims 1 to 3 wherein R$^{11}$ represents a hydrogen atom, a methyl group or an ethyl group 6. The $\Delta^7$-prostaglandin E of claim 1 which is represented by the following formula

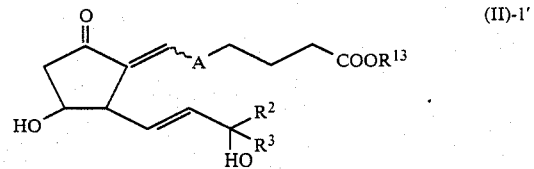

wherein R$^2$, R$^3$ and A are as defined, and R$^{13}$ represents a hydrogen atom, a methyl group or an ethyl group.

7. The $\Delta^7$-prostaglandin E of claim 1 wherein the tri(C$_{1-7}$ hydrocarbon)silyl group is a tri(C$_1$–C$_4$ alkyl)silyl group, a diphenyl (C$_1$–C$_4$)silyl group or a tribenzylsilyl group.

8. The $\Delta^7$-prostaglandin E of claim 1 wherein the protective group capable of forming an acetal linkage with the oxygen atom of the hydroxyl group is a compound selected from the group consisting of methoxyethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl, and 6,6-dimethyl-3-oxa-2-oxo-bicyclo [3.1.0] hex-4-yl groups.

9. The $\Delta^7$-prostaglandin E of claim 1 which is a $\Delta^7$-prostaglandin E$_1$.

10. The $\Delta^7$-prostaglandin E of claim 9 which is selected from the group consisting of $\Delta^7$-PGE$_1$, $\Delta^7$-16-methyl PGE$_1$, $\Delta^7$-16,16-dimethyl PGE$_1$, $\Delta^7$-20-methyl PGE$_1$, $\Delta^7$-17,20-dimethyl PGE$_1$, $\Delta^7$-16,17,18,19,20-pentanor-15-cyclopentyl PGE$_1$, $\Delta^7$-16,17,18,19,20-pentanor-15-cyclohexyl PGE$_1$, $\Delta^7$-15-methyl PGE$_1$, $\Delta^7$-17,17,20-trimethyl PGE$_1$, and $\Delta^7$-17,18,19,20-tetranor-16-cyclohexyl PGE$_1$.

11. The $\Delta^7$-prostaglandin E of claim 1 which is a $\Delta^7$-prostaglandin E$_2$.

12. The $\Delta^7$-prostaglandin E of claim 11 which is selected from the group consisting of $\Delta^7$-PGE$_2$, $\Delta^7$-16-methyl PGE$_2$, $\Delta^7$-16,16-dimethyl PGE$_2$, $\Delta^7$-20-methyl PGE$_2$, $\Delta^7$-17,20-dimethyl PGE$_2$, $\Delta^7$-16,17,18,19,20-pentanor-15-cyclopentyl PGE$_2$, $\Delta^7$-16,17,18,19,20-pentanor-15-cyclohexyl PGE$_2$, $\Delta^7$-15-methyl PGE$_2$, $\Delta^7$-17,17,20-trimethyl PGE$_2$, $\Delta^7$-17,18,19,20-tetranor-16-cyclohexyl PGE$_2$, $\Delta^7$-5,6-dehydro-PGE$_2$, $\Delta^7$-5,6-dehydro-16-methyl PGE$_2$, $\Delta^7$-5,6-dehydro-16,16-dimethyl PGE$_2$, $\Delta^7$-5,6-dehydro-20-methyl PGE$_2$, $\Delta^7$-5,6-dehydro-17,20-dimethyl PGE$_2$, $\Delta^7$-5,6-dehydro-16,17,18,19,20-pentanor-15-cyclopentyl PGE$_2$, $\Delta^7$-5,6-dehydro-16,17,18,19,20-pentanor-15-cyclohexyl PGE$_2$, $\Delta^7$-5,6-dehydro-15-methyl PGE$_2$, $\Delta^7$-5,6-dehydro-17,17,20-trimethyl PGE$_2$, $\Delta^7$-5,6-dehydro-18-oxa PGE$_2$, and $\Delta^7$-5,6-dehydro-17,18,19,20-tetranor-16-cyclopentyl PGE$_2$.

* * * * *